(12) United States Patent
Salem et al.

(10) Patent No.: US 10,941,128 B2
(45) Date of Patent: *Mar. 9, 2021

(54) THYMOQUINONE DERIVATIVES FOR TREATMENT OF CANCER

(71) Applicant: United Arab Emirates University, Al Ain (AE)

(72) Inventors: Alaa Eldin Salem, Al Ain (AE); Ismail El Haty, Al Ain (AE); Ibrahim Abdou, Al Ain (AE); Abdu Adem, Al Ain (AE); Samir Attoub, Al Ain (AE)

(73) Assignee: United Arab Emirates University, Al Ain (AE)

( * ) Notice: Subject to any disclaimer, the term of this patent is extended or adjusted under 35 U.S.C. 154(b) by 0 days.

This patent is subject to a terminal disclaimer.

(21) Appl. No.: 16/598,430

(22) Filed: Oct. 10, 2019

(65) Prior Publication Data

US 2020/0031788 A1 Jan. 30, 2020

Related U.S. Application Data

(63) Continuation of application No. 15/502,944, filed as application No. PCT/IB2014/063821 on Aug. 9, 2014, now Pat. No. 10,501,428.

(51) Int. Cl.

| C07D 295/13 | (2006.01) |
|---|---|
| C07C 225/28 | (2006.01) |
| A61P 35/00 | (2006.01) |
| A61K 31/122 | (2006.01) |
| A61K 31/5375 | (2006.01) |
| A61K 45/06 | (2006.01) |
| C07C 221/00 | (2006.01) |

(52) U.S. Cl.
CPC .......... *C07D 295/13* (2013.01); *A61K 31/122* (2013.01); *A61K 31/5375* (2013.01); *A61K 45/06* (2013.01); *A61P 35/00* (2018.01); *C07C 221/00* (2013.01); *C07C 225/28* (2013.01)

(58) Field of Classification Search
CPC ............................ C07C 225/28; C07D 295/13
See application file for complete search history.

(56) References Cited

U.S. PATENT DOCUMENTS

| 2001/0031864 A1 | 10/2001 | Kaul et al. |
| 2017/0283366 A1 | 10/2017 | Salem et al. |
| 2017/0334871 A1 | 11/2017 | Salem et al. |

FOREIGN PATENT DOCUMENTS

| WO | 2011/126544 A2 | 10/2011 |
| WO | 2013/012886 A1 | 1/2013 |

OTHER PUBLICATIONS

Mure et al. (J. Am. Chem. Soc., 1995, 117, 8698-8706).*
Mujahid Yusufi et al., "Synthesis, characterization and anti-tumor activity of novel thymoquinone analogs against pancreatic cancer," Bioorganic & Medicinal Chemistry Letters, 23 (2013) 3101-3104.
Minae Mure et al., "Model Studies of Topaquinone-Dependent Amine Oxidases. 1. Oxidation of Benzylamine by Topaquinone Analogs," J. Am. Chem. Soc., 1995, 117, 8698-8706.
Katharina Effenberger et al., "Terpene Conjugates of the *Nigella sativa* Seed-Oil Constituent Thymoquinone with Enhanced Efficacy in Cancer Cells," Chemistry & Biodiversity, vol. 7, 2010, 129-139.
Samir Attoub et al., "Thymoquinone as an anticancer agent: evidence from inhibition of cancer cells viability and invasion of in vitro and tumor grown in vivo," Fundamental & Clinical Pharmacology, 27 (2013) 557-569.
International Search Report and Written Opinion of International Application No. PCT/IB2014/063821, dated Dec. 17, 2014, 9 pages.
Hala Gali-Muhtasib et al., "Thymoquinone: A promising anticancer drug from natural sources," Int'l J. Biochemistry & Cell Biology, 38 (2006) 1249-1253.
Bharat B. Aggarwal et al., "Potential of Spice-Derived Phytochemicals for Cancer Prevention," Planta Med, 2008, 74, 1560-1569.
Chern Chiuh Woo et al., "Thymoquinone: Potential cure for inflammatory disorders and cancer," Biochemical Pharmacology, 83 (2012) 443-451.
Mohamed Labib Salem, "Immunomodulatory and therapeutic properties of the *Nigella sativa* L. seed," International Immunopharmacology, 5 (2005) 1749-1770.
Subhash Padhye et al., "From here to eternity—the secret of Pharaohs: Therapeutic potential of black cumin seeds and beyond," Cancer Ther., 2008; 6(b): 495-510.
André Wirries et al., "Thymoquinone hydrazone derivatives cause cell cycle arrest in p53-competent colorectal cancer cells," Experimental and Therapeutic Medicine, 1, 2010, 369-375.
David R. Worthen et al., "The in Vitro Anti-tumor Activity of Some Crude and Purified Components of Blackseed, *Nigella sativa* L.," Anticancer Research, 1998, 18, 1527-1532.
Sarah Burge et al., "Survey and Summary Quadruplex DNA: sequence, topology and structure," Nucleic Acids Research, 2006, vol. 34, No. 19, 5402-5415.
Attila Ambrus et al., "Human telomeric sequence forms a hybrid-type intramolecular G-quadruplex structure with mixed parallel/antiparallel strands in potassium solution," Nucleic Acids Research, 2006, vol. 34, No. 9, 2723-2735.

(Continued)

Primary Examiner — Susanna Moore
(74) Attorney, Agent, or Firm — Fitch, Even, Tabin & Flannery LLP

(57) ABSTRACT

The present invention describes thymoquinone compounds formula (I): (i) These compounds have been identified as being useful in the treatment of cancer.

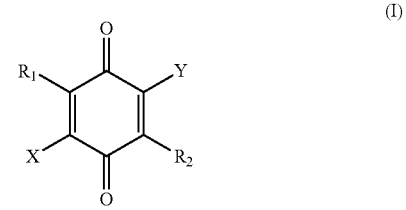

19 Claims, 18 Drawing Sheets
Specification includes a Sequence Listing.

(56) References Cited

OTHER PUBLICATIONS

Viktor Viglasky et al., "Evaluation of Human Telomeric G-Quadruplexes: The Influence of Overhanging Sequences on Quadruplex Stability and Folding," Journal of Nucleic Acids, vol. 2010, Article ID 820356, 8 pages.
Julian Leon Huppert, "Four-stranded DNA: cancer, gene regulation and drug development," Phil. Trans. R. Soc. A, (2007) 365, 2969-2984.
Martin Read et al., "Structure-based design of selective and potent G quadruplex-mediated telomerase inhibitors," PNAS, Apr. 24, 2001, vol. 98, No. 9, 4844-4849.
A.E.M. Saeed et al., "Synthesis of some 2,5-diamino-3,6-dibromo-1,4-benzoquinones," African Journal of Pure and Applied Chemistry, vol. 3 (12), pp. 275-280, Dec. 2009.
A.S. Hammam et al., "Synthesis of New Triphenodithiazine- and Indolocarbazolediones of Biological Interest," Chem. Pap., 61 (4) 292-299 (2007).
Ignatious Abraham et al., "Recent Advances in 1,4-Benzoquinone Chemistry," J. Braz. Chem. Soc., vol. 22, No. 3, 385-421, 2011.
Junko Koyama, "Anti-Infective Quinone Derivatives of Recent Patents," Frontiers in Anti-Infective Drug Discovery, 2010, 1, 294-322.
Sanjeev Banerjee et al., Review on Molecular and Therapeutic Potential of Thymoquinone in Cancer, Nutrition and Cancer, 62:7, Oct. 4, 2010, 938-946.
Eugene Zavarin, "On the Structure of the Photodimer of Thymoquinone," J. Org. Chem, 1958, 23(1): 47-50.
Ralph M. Hixon, "A Study of Amino and Oximo Derivatives of Thymoquinone," J. Am. Chem. Soc., 1923, vol. 45 (10): 2333-2341.
Harold W. Moore et al., "Rearrangement of Azidoquinones. Reaction of Thymoquinone and 2,5-Dimethyl-1,4-benzoquinone with Sodium Azide in Trichloroacetic Acid," The Journal of Organic Chemistry, vol. 33, No. 11, Nov. 1968, 4019-4024.
Sandry Breyer et al., "Effects of Thymoquinone—Fatty Acid Conjugates on Cancer Cells," ChemMedChem, 2009, 4, 761-768.
Katharina Effenberger-Neidnicht et al., "Cellular Localisation of Antitumoral 6-Alkyl Thymoquinones Revealed by an Alkyne—Azide Click Reaction and the Streptavidin—Biotin System," ChemBioChem, 2011, 12, 1237-1241.
Jia-Heng Tan et al., "Design of Selective G-quadruplex Ligands as Potential Anticancer Agents," Mini-Reviews in Medicinal Chemistry, 2008, 8, 1163-1178.
Christopher M. Incles et al., "Telomerase inhibitors in cancer therapy: Current status and furure directions," Current Opinion in Investigational Drugs, 2003 4(6) (12 pages).
Anthony R. Amaro et al., "Metabolic Activation of PCBs to Quinones: Reactivity toward Nitrogen and Sulfur Nucleophiles and Influence of Superoxide Dismutase," Chem. Res. Toxicol., 1996, 9, 623-629.
Héléne Bertrand et al., "The importance of metal geometry in the recognition of G-quadruplex-DNA by metal-terpyridine complexes," Organic & Biomolecular Chemistry, 2007, 5, 2555-2559.
Anna Arola et al., "Stabilisation of G-Quadruplex DNA by Small Molecules," Current Topics in Medicinal Chemistry, 2008, vol. 8, No. 15, 1405-1415.
Xue Li et al., "Synthesis and anti-breast cancer activity of new indolylquinone derivatives," European Journal of Medicinal Chemistry, 54 (2012) 42-48.
Sanjeev Banerjee et al., "Structure-Activity Studies on Therapeutic Potential of Thymoquinone Analogs in Pancreatic Cancer," Pharm. Res., (2010) 27:1146-1158.
Manoj Batra et al., "An efficient synthesis and biological activity of substituted p-benzoquinones," Bioorganic & Medicinal Chemistry, 14 (2006) 8519-8526.
Ahn Tuân Phan, "Human telomeric G-quadruplex: structures of DNA and RNA sequences," FEBS Journal, 277 (2010) 1107-1117.
Graham D. Balkwill et al., "Folding Topology of a Bimolecular DNA Quadruplex Containing a Stable Mini-hairpin Motif within the Diagonal Loop," J. Mol. Biol., (2009) 385, 1600-1615.
Jyotirmayee Dash et al., "Synthesis of Bis-indole Carboxamides as G-Quadruplex Stabilizing and Inducing Ligands," Chem. Eur. J., 2012, 18, 554-564.
Marie-Paule Teulade-Fichou et al., "Selective Recognition of G-Quadruplex Telomeric DNA by a Bis (quinacridine) Macrocycle," J. Am. Chem. Soc., 2003, 125, 4732-4740.
Abraham E. Mathew et al., "Amino-Substituted p-Benzoquinones," J. Med. Chem., 1986, 29, 1792-1795.
Yan Xu et al., "The new models of the human telomere d[AGGG(T-TAGGG)3] in K+ solution," Bioorg. Med. Chem., 14 (2006) 5584-5591.
Daniel Khananshvili et al., "Demonstration of two binding sites for ADP on the isolated ß-subunit of the Rhodospirillum rubrum R1F0F1-ATP synthase," FEBS 2031, vol. 178, No. 1, Dec. 1984, 10-14.
Tai-Shun Lin et al., "Synthesis and Antimalarial Activity of 2-Aziridinyl- and 2,3-Bis(aziridinyl)-1,4-naphthoquinonySlulfonate and Acylate Derivatives," J. Med. Chem., 1991,34, 1634-1639.
M.J. Cuéllar et al., "Topical anti-inflammatory activity of some Asian medicinal plants used in dermatological disorders," Fitoterapia, 72 (2001) 221-229.
Paul Dowd et al., "On the mechanism of the anticlotting action of vitamin E quinone," Proc. Natl. Acad. Sci. USA, vol. 92, pp. 8171-8175, Aug. 1995.
Sunil Sagar et al., "Pro-apoptotic activities of novel synthetic quinones in human cancer cell lines," Cancer Letters, 285 (2009) 23-27.
Carmen Petronzi et al., Cyclohexa-2,5-diene-1,4-dione-based antiproliferative agents: design, synthesis, and cytotoxic evaluation, Journal of Experimental & Clinical Cancer Research 2013, 32:24 (10 pages).
Cele Abad-Zapatero, et al., "Ligand Efficiency Indices as Guideposts for Drug Discovery." Drug Discovery Today, Apr. 2005, vol. 10, No. 7, pp. 464-469.
James D. Adkins, et al., "Potential Aminoquinone Inhibitors of Ce and BMI/carbon Fiber/Aluminum Composite Galvanic Degradation." International SAMPE Technical Conference, 2001, vol. 33, pp. 911-923, Abstract only.
Michael R. Boyd. "The NCI In Vitro Anticancer Drug Discovery Screen." Anticancer Drug Development Guide: Preclinical Screening, Clinical Trials, and Approval, Ed. Beverly A. Teicher, Humana Press, 1997, pp. 23-42.
Angelika M. Burger, et al. "Preclinical Screening for New Anticancer Agents." Handbook of Anticancer Pharmacokinetics and Pharmacodynamics. Edited by William D. Figg, Howard L. McLeod, Cancer Drug Discovery and Development, 2004, Humana Press Inc., Totowa, New Jersey, pp. 29-44.
Sachin Kumar, et al., "Preclinical Screening Methods in Cancer." Indian Journal of Pharmacology, Sep.-Oct. 2016, vol. 48, No. 5, pp. 481-486, 10 pages.
Kylie A. Macgregor, et al., "Development of Quinone Analogues as Dynamin GTPase Inhibitors." European Journal of Medicinal Chemistry, 2014, vol. 85, pp. 191-206.
Kobaisy Mozaina, et al., "Activity of 1,4-Benzoquinones Against Formosan Subterranean Termites (*Coptotermes formosanus*)." Journal of Agricultural and Food Chemistry, 56 (2008), 4021-4026.
Bhupesh S. Samant, et al., "Novel Naphthoquinone Derivatives: Synthesis and Activity Against Human African Tryanosomiasis." Bioorganic & Medicinal Chemistry Letters, 2013, vol. 23, pp. 1420-1423.
Hatice Yildirim, et al., "2,3-Disubstituted-1,4-naphthoquinones Containing an Arylamine with Trifluoromethyl Group:Synthesis, Biological Evaluation, and Computational Study." The Royal Society of Chemistry, 2017, vol. 7, pp. 25753-25764.
Zhong-Lu You, et al., "Synthesis, Biological Evaluation, and Molecular Docking Studies of 2,5-substituted-1,4-Benzoquinone as Novel Urease Inhibitors." Bioorganic & Medicinal Chemistry, 2012, vol. 20, pp. 4889-4894.

\* cited by examiner

THYMOQUINONE DERIVATIVES FOR TREATMENT OF CANCER

CROSS REFERENCE TO RELATED APPLICATIONS

This application is a continuation application of U.S. application Ser. No. 15/502,944 filed on Feb. 9, 2017, which is a U.S. national phase application of International Patent Application No. PCT/IB2014/063821, filed Aug. 9, 2014, the contents of which are incorporated herein by reference in their entireties.

TECHNICAL FIELD

This invention relates to substituted thymoquinone derivatives. The invention also relates to the use of such compounds in the treatment of cancer and pharmaceutical compositions containing such compounds.

SEQUENCE LISTING

This application contains a sequence listing. The sequence listing file in ASCII text format is named Sequence_Listing_140943_ST25.txt, is 876 bytes in size, was created on Jun. 19, 2017, and is incorporated herein by reference in its entirety.

BACKGROUND ART

Thymoquinone, 2-isopropyl-5-methyl-1,1,4-benzoqinone (TQ), can be extracted from black seed (Nigella sativa) oil and has been reported as an anticancer agent in cancer cells. The anticancer effects of TQ on malignant tumours with selectivity towards cancer cells over normal cell has been discussed in Aggarwall BB et al (2008) Planta Med vol. 74(13) pp 1560-1569. Thymoquinone analogs have also been proposed for the use in treating pancreatic cancers, for example in WO2011126544.

The end caps of human chromosomes, telomeres, are known to protect DNA chromosomes against degradation, non-homologous end-stacking and nuclease attacks. Telomeres are shortened after each cell division till the cell loses its functions and apotosis. The telomerase enzyme, found active in most cancer cells, re-elongates the telomere and maintains its length causing cancer cell to continue to divide indefinitely. Telomeres comprise tandem repeats enriched in guanine bases that fold up in physiological conditions to form four-stranded DNA called G-quadruplex. Folding single stranded telomeric DNA into G-quadruplex structure has been shown to inhibit the telomerase enzyme, overexpressed in cancer cells.

Small molecules that bind and stabilise G-quadruplex DNA have been found to inhibit the telomerase enzyme in cancer cells and subsequently inhibit DNA replication and cancer cell proliferation, Huppert JL (2007), Phil. Trans. A. Math. Phys. Eng. Sci., vol. 365(1861) pp 2969-2984. Therefore molecules with high preferential affinity towards G-quadruplex DNA have been seen as a potential avenue of compounds for developing new anticancer therapeutic agents.

Accordingly it is an object of the invention to provide further thymoquinone derivatives that may be effective in cancer treatment.

SUMMARY OF INVENTION

The present invention relates to compounds of formula (I):

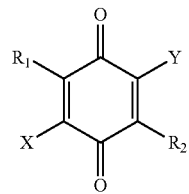

and to pharmaceutically salts or solvates thereof wherein:

$R_1$ and $R_2$ are independently selected from $C_1$-$C_6$ alkyl, wherein $R_1$ and $R_2$ are different;

X is $NR_3R_4$, wherein:

$R_3$ is selected from H or —$(CH_2)_2$—OH; and $R_4$ is selected from H or —($C_1$-$C_4$alkyl)$R_5$, wherein:

$R_5$ is selected from:

a) —OH, b) phenyl, wherein phenyl is optionally substituted by 1-3 substituents independently selected from —$CF_3$, —F, —$OCH_3$, —$NH_2$ and —$SO_2NH_2$, c) a 5 or 6 membered heterocyclic ring having 1 or 2 hetero atoms selected from O and N, and wherein the heterocyclic ring is optionally substituted by 1-2 substituents independently selected from —OH and $CH_3$, d) a ring system having the formula of:

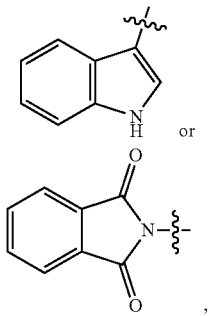

and e) $NR_6R_7$, wherein:

$R_6$ is selected from H or $CH_3$; and $R_7$ is selected from $CH_3$, phenyl, and a ring system having the formula of:

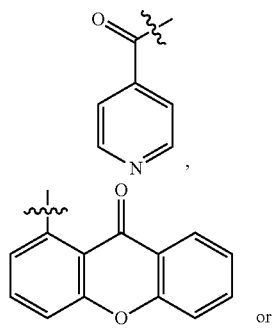

3
-continued

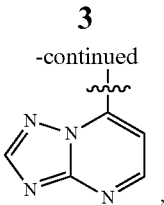

wherein the ring system is optionally substituted by 1-2 substituent of CH$_3$; and Y is H.

In a preferred embodiment R$_1$ is CH$_3$, or isopropyl. More preferably R$_1$ is CH$_3$.

In a preferred embodiment R$_2$ is CH$_3$, or isopropyl. More preferably R$_2$ is isopropyl.

In a particularly preferred embodiment R$_1$ is CH$_3$ and R$_2$ is isopropyl.

In a preferred embodiment R$_3$ is H.

In a preferred embodiment R$_4$ is —(C$_1$-C$_4$alkyl)R$_5$. More preferably R$_4$ is —(C$_1$-C$_2$alkyl)R$_5$.

In a preferred embodiment R$_5$ is selected from:
a) —OH,
b) phenyl, wherein phenyl is optionally substituted by 1-3 substituents independently selected from —CF$_3$, —F, —OCH$_3$, —NH$_2$ and —SO$_2$NH$_2$,
c) a 5 or 6 membered heterocyclic ring selected from morpholinyl, pyranyl, piperidinyl, pyrrolidinyl, piperazinyl, pyridinyl, and pyrimidinyl, wherein the heterocyclic ring is optionally substituted by 1-2 substituents independently selected from —OH and CH$_3$.
d) a ring system having the formula of:

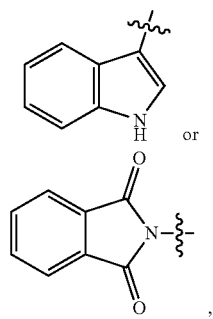

and
e) NR$_6$R$_7$, wherein:
R$_6$ is selected from H or CH$_3$; and
R$_7$ is selected from CH$_3$, phenyl, and a ring system having the formula of:

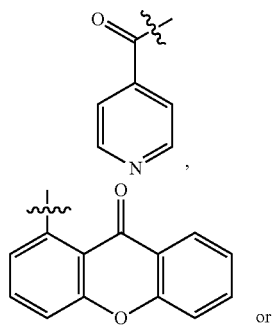

4
-continued

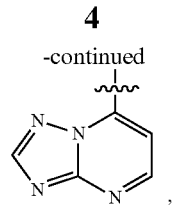

wherein the ring system is optionally substituted by 1-2 substituent of CH$_3$.

In one embodiment wherein R$_5$ is a 5 or 6 membered heterocyclic ring, the 5 or 6 membered heterocyclic ring is selected from morpholinyl, pyranyl, piperidinyl, pyrrolidinyl, piperazinyl, each optionally substituted by —OH or the heterocyclic ring is selected from pyridinyl, and pyrimidinyl, wherein the pyrimidinyl is optionally substituted with —OH and CH$_3$.

In a particularly preferred embodiment R$_4$ is H or —(C$_1$-C$_2$alkyl)R$_5$, wherein R$_5$ is selected from OH, morpholinyl and phenyl, wherein the phenyl is optionally substituted with 1 or 2 substituents selected from —CF$_3$, —F and —OCH$_3$.

In one embodiment when R$_3$ is H, R$_4$ is preferably H or —(C$_1$-C$_2$alkyl)R$_5$, wherein R$_5$ is selected from morpholinyl and phenyl, wherein the phenyl is optionally substituted with 1 or 2 substituents selected from —CF$_3$, —F and —OCH$_3$.

Particularly preferred compounds of the invention include:
5-Isopropyl-2-methyl-3-((2-morpholinoethyl)amino)-1,4-benzoquinone
5-Isopropyl-2-methyl-3-(4-trifluoromethylbenzylamino)-1,4-benzoquinone
5-Isopropyl-2-methyl-3-(4-fluorobenzylamino)-1,4-benzoquinone
5-Isopropyl-2-methyl-3-(benzylamino)-1,4-benzoquinone
5-Isopropyl-2-methyl-3-(3,5-ditrifluoromethylbenzylamino)-1,4-benzoquinone
5-isopropyl-2-methyl-3-(2-hydroxyethylamino)-1,4-benzoquinone
5-isopropyl-2-methyl-3-(3,4-dimethoxylbenzylamino)-1,4-benzoquinone
3-amino-5-isopropyl-2-methyl-1,4-benzoquinone.

A particularly preferred compound is 3-amino-5-isopropyl-2-methyl-1,4-benzoquinone.

Suitable salts include salts of acidic or basic groups present in compounds of formula (I). The compounds of formula (I) that are basic in nature are capable of forming a wide variety of salts with various inorganic and organic acids. The acids that may be used to prepare pharmaceutically acceptable acid addition salts of such basic compounds of formula (I) are those that form non-toxic acid addition salts. Suitable salts include acetate, benzensulfonate, benzoate, bicarbonate, bisulfate, bitartrate, borate, bromide, calcium edentate, camsylate, carbonate, chloride, clavulanate, citrate, dihydrochloride edentate, edisylate, estolate, esylate, ethylsuccinate, fumarate, gluceptate, gluconate, glutamate, glycollylarsanilate, hexylresorcinate, hydrabamine, hydrobromide, hydrochloride, iodide isothionate, lactate, lactobionate, laurate, malate, maleate, mandelate, mesylate, methylsulfate, mucate, napsylat, nitrate, oleate, oxalate, pamoate, palmitate, pantothenate, phosphate, diphosphate, diphosphate, polygalacturonate, salicylate, stearate, subacetate, succinate, tannate, tartrate, teoclate, tosylate and valerate.

The compounds of the present invention may be synthesised by a number of synthetic routes. In one method of making the compounds of the invention, thymoquinone derivatives can be synthesised as shown in Scheme I, wherein $R_1$, $R_2$, $R_3$ and $R_4$ are defined herein.

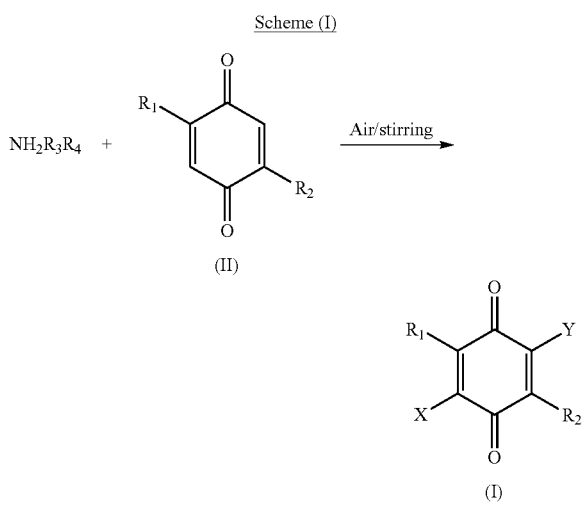

Compounds of formula (1) may be synthesised in a one pot reaction by reacting thymoquinone in a suitable solvent such as methanol, with the appropriate amine, $NH_2R_3R_4$, dissolved in a suitable solvent. The mixture is reacted in the presence of air at room temperature. The solvent is then concentrated and purified and the resultant products are crystallized.

An alternative route for synthesising a thymoquinone derivative of formula (III) is shown in scheme (II).

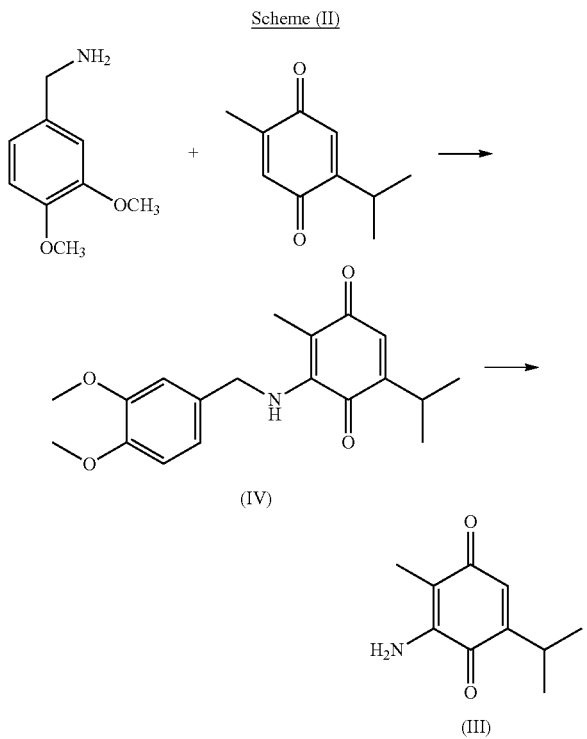

Compounds of formula (III) may be synthesised by reacting thymoquinone with dimethoxybenzylamine in a solvent, such as methanol. The mixture is reacted in the presence of air at room temperature resulting in the formation of a compound of formula (IV). The mixture is allowed to decompose and a product of formula (III) is formed. The solvent is then concentrated and purified and the resultant product is crystallised.

These compounds have been found to selectively bind G-quadruplex DNA and stabilise their structure. Stabilisation of the G-quadruplex structure can inhibit the telomerase enzyme, and therefore the compounds may play a role in the treatment of cancer.

The invention also relates to compounds of formula (I) as described above for use in the treatment of cancer. In particular the compounds are particularly useful in the treatment of pancreatic cancer, lung cancer, prostate cancer and breast cancer.

The invention also provides a method of treating cancer in a mammal, particularly a human, comprising administering to the mammal an amount of a compound of formula (I) as defined above, or a pharmaceutically acceptable salt or solvate thereof. The compound may be administered in a therapeutically effective amount.

The invention further relates to the compounds of formula (I) in combination with at least one suitable anti-tumour or neoplastic agent for the treatment of cancer, in particular for the treatment of pancreatic, lung, prostate or breast cancer.

The term "treatment" is intended to include curing, reversing, alleviating, palliative and prophylactic treatment of the condition.

A "therapeutically effective amount" of a compound is an amount of the compound, which when administered to a subject, is sufficient to confer the intended therapeutic effect. A therapeutically effective amount can be given in one or more administrations.

Common cancers would include, bladder, breast, colon, rectal, endometrial, kidney (renal cell), leukaemia, lung, melanoma, non-Hodgkin lymphoma, pancreatic, prostate, brain, skin, liver and thyroid cancers.

Patients suffering from cancer are commonly co-administered additional therapeutic agents, in particular suitable antineoplastic or anti-tumour agents. Suitable co-administrants would include:
1. Alkylating antineoplastic agents: such as cisplatin, carboplatin, oxaliplatin, mechlorethamine, cyclophosphamide, chlorambucil, and ifosfamide.
2. Plant alkaloids and terpenoids. These include:
   i. vinca alkaloids such as vincristine, vinblastine, vinorelbine and vindesine
   ii. podophyllotoxins such as etoposide and teniposide
   iii. taxanes, such as paclitaxel, originally known as taxol, and docetaxel.
3. Topoisomerase inhibitors:
   i. type I topoisomerase inhibitors include camptothecins: irinotecan and topotecan
   ii. type II inhibitors include amsacrine, etoposide, etoposide phosphate, and teniposide
4. Cytotoxic antibiotics such as actionmycin, anthracyclins, doxorubicin, daunorubicin, valrubicin and epirubicin. Other cytoxic antibiotics include bleomycin, plicamycin and mitomycin.

Other therapeutic agents are commonly administered to patients to deal with the side effects of chemotherapy. Such agents might include anti-emetics for nausea, or agents to treat anaemia and fatigue. Other such medicaments are well known to physicians and those skilled in cancer therapy.

Such agents may be administered sequentially, simultaneously or concomitantly.

The invention also relates to a pharmaceutical composition comprising a compound of formula (I) as described above, or a pharmaceutically acceptable salt or solvate thereof and a pharmaceutically acceptable diluents or carrier.

The pharmaceutical composition may comprise an additional therapeutic agent.

Suitable composition forms include forms suitable for oral administration such as tablets, capsule, pills, powders, sustained release formulations, solutions, and suspension, for parental injection such as sterile saline solutions, suspensions or emulsion; for topical administration such as ointments or creams; or rectal administration such as suppositories.

Exemplary parenteral administration forms include suspensions or solutions in sterile aqueous solutions, for example aqueous propylene glycol or dextrose solutions. Such dosage forms can be suitably buffered, if desired.

Suitable pharmaceutical carriers include inert diluents or fillers, water and various organic solvents. Compositions may also include additional ingredients such as flavouring, binders, and excipients. Tablets may include: disintegrates such as starch, alginic acid and complex silicates; binding agents such as sucrose, gelatine and acacia, and lubricating agents such as magnesium stearate, sodium lauryl sulphate and talc.

Solid compositions may also include soft and hard gelatin capsules. Preferred materials include lactose, milk sugars and high molecular weight polyethylene glycols.

Aqueous suspensions or elixirs may include sweetening or flavouring agents, colours and dyes, emulsifying agents, suspending agents as wells as diluents such as water, ethanol, propylene glycol, glycerin or combinations thereof.

Pharmaceutical forms suitable for the delivery of the compounds of the present invention and methods of preparing the various pharmaceutical compositions will be readily apparent to those skilled in the art. Such compositions and methods for their preparations may be found, for example in Remington's Pharmaceutical Sciences, 19$^{th}$ Edition (Mack Publishing Company 1995).

FIGURES

FIGS. 1A and 1B shows inhibition of cellular viabilities by compounds TQ 1-5 in A540 cells (FIG. 1A) and TQ8 in A549, MDA-MB-231, and HT29 cells (FIG. 1B). Cells were treated at the indicated concentrations of compounds TQ 1-5 and 8 or with vehicle (0.1% DMSO) as a control. Columns, mean; bars S.E.M.

FIG. 2 shows fluorescence titrations of compounds TQ1-8 (5×10−6M) (a-h respectively) with G-quadruplex. TQs were excited at 279, 280, 280, 278, 280, 280, 280 and 327 nm respectively with 10 nm slits width. The inset represents a plot for fluorescence titrations using modified Scatchard equation.

EXPERIMENTAL

Figure 1A:
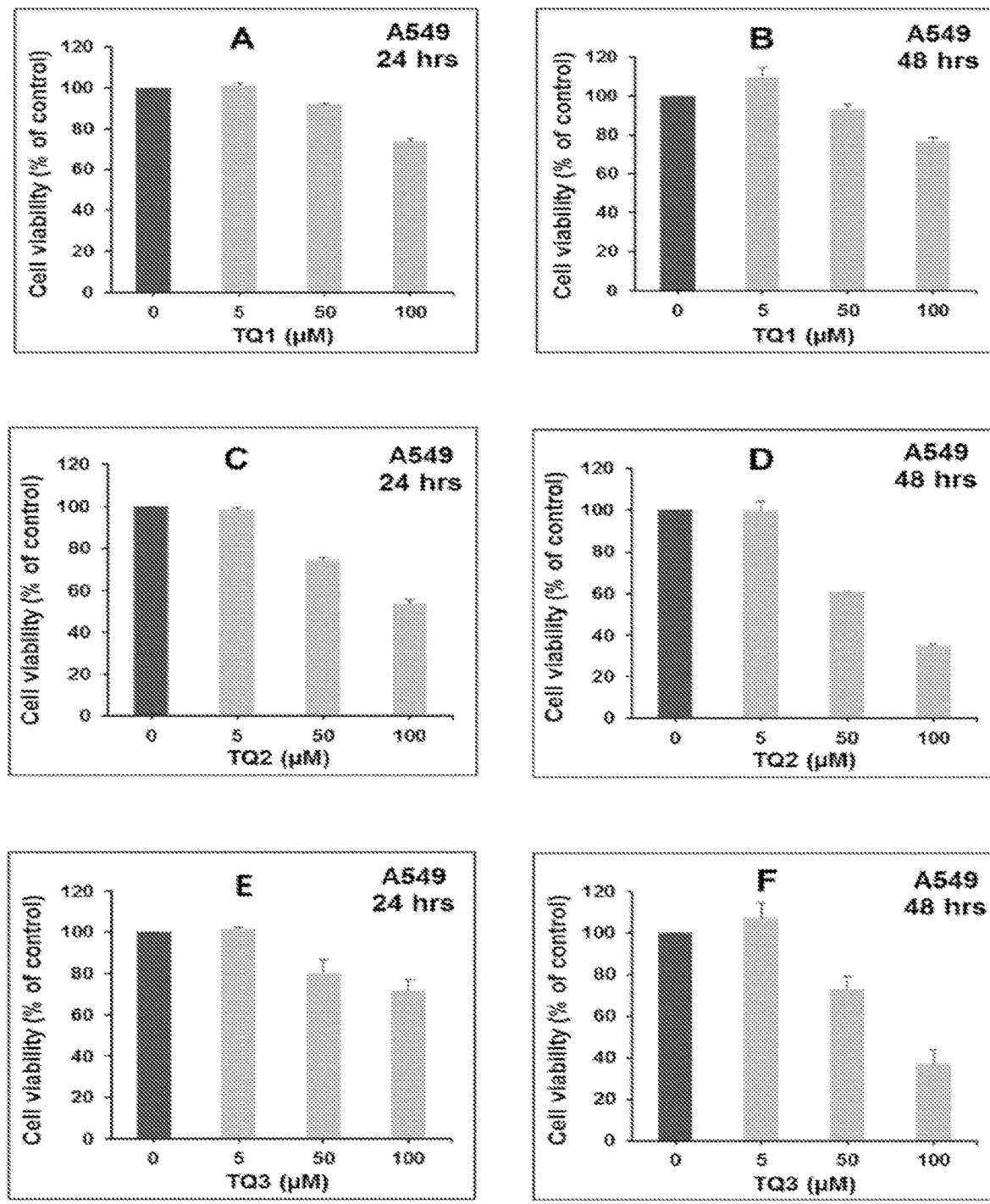
Figure 1A:
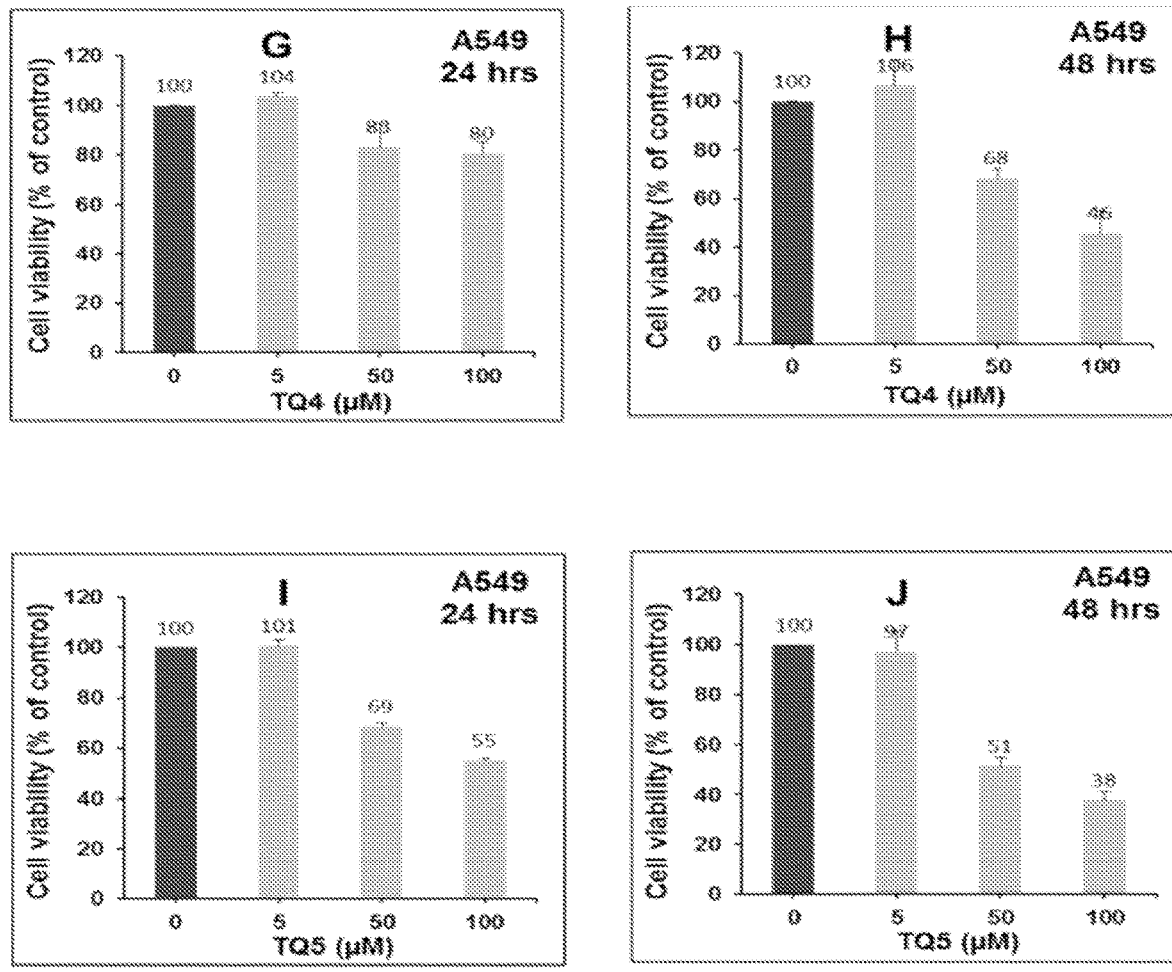

The synthesis of various compounds of the present invention is described by way of example.

Synthesis of Thymoquinone Derivatives 5 mmol thymoquinone (821 mg) (Frinton Laboratories Inc, USA) was dissolved in methanol (50 mL) into a two necks flask (100 mL). The amine solution (5 mmol), (2-aminoethylmorpholine, benzylamine, 4-(trifluoromethyl) benzylamine, 3,5-bis(trifluoromethyl)benzylamine, 3,4-dimethoxybenzylamine, 4-fluorobenzyl-amine or 2-aminoethanol (Sigma-Aldrich)), dissolved in methanol (5 mL), was added drop wise to the thymoquinone solution.

The reaction mixture was stirred and air bubbled at room temperature for up to 3 days during which the reaction progress was monitored using TLC. The solvent was concentrated under vacuum and the product was purified on silica gel column using hexane:ethyl acetate (6:4 v/v) as mobile phase.

This general procedure was applied for the synthesis of compounds TQ1-TQ7. Compound 3-aminothymoquinone (TQ8) was prepared as described below.

3-aminothymoquinone (TQ8) was synthesized by allowing thymoquinone (5 mmol, 821 mg) to react with 3,4-dimethoxybenzylamine (5 mmol, 777 μL) in methanol (5 mL) as per the procedure above. The solution was stirred and air bubbled at room temperature for 5 days during which the reaction was monitored by TLC.

Initially, 3',4-dimethoxybenzylamino-thymoquinone (TQ7) is formed and then hydrolyzed to form 3-aminothymoquinone (TQ8). Oxidation of 3',4-dimethoxybenzylamino-thymoquinone (TQ7) results in the formation of the hydroxymethyl-amino intermediate which upon rearrangement produced 3-aminothymoquinone (TQ8) and 3,4-dimethoxybenzaldehyde.

The solvent was concentrated under vacuum followed by purifying the product over silica gel column using hexane: ethyl acetate (7:3 v:v) as mobile phase. The pink layer was separated into two layers, the first released is for TQ7 and the second released is for TQ8. $R_f$ for the compound TQ8 is 0.662.

The mechanism for the formation of 3-aminothymoquinone (TQ8) is shown in Scheme (III).

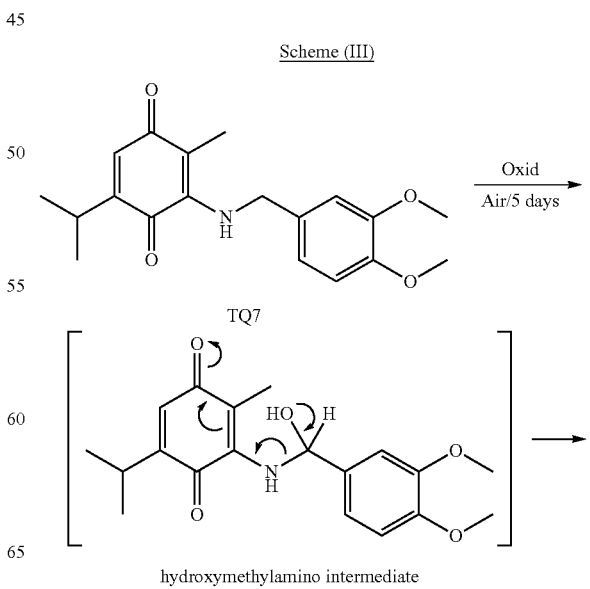

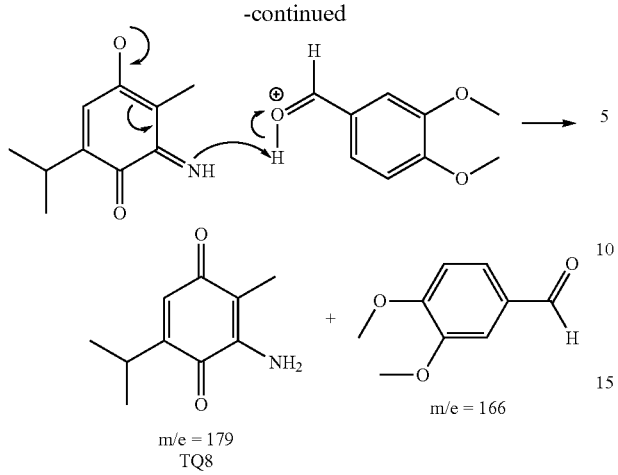

m/e = 179
TQ8 m/e = 166

The obtained products were crystallized from the same solvent and their structure was confirmed using IR, $^1$H-NMR and $^{13}$C-NMR, MS spectrometry and elemental analysis. Table 1 shows the reaction times, melting points and reaction yields of the newly synthesized thymoquinone amine derivatives.

Reaction times between 24 hours and 5 days were found necessary for different products with melting temperatures of 68-114° C. and reaction yields between 45.2-73.8% obtained.

TABLE 1

| Compound | Aryl-amine | Reaction Time | M.P. ° C. | Yield |
|---|---|---|---|---|
| TQ1 | (morpholinoethyl) | 48 hrs | 92-95 | 68.3% |
| TQ2 | (4-CF₃ benzyl) | 64 hrs | 110.5-112 | 50.1% |
| TQ3 | (4-F benzyl) | 72 hrs | 80-82.5 | 45.2% |
| TQ4 | (benzyl) | 72 hrs | 83-84.5 | 73.6% |
| TQ5 | (3,5-di-CF₃ benzyl) | 48 hrs | 111-114 | 47.2% |
| TQ6 | (hydroxypropyl) | 36 hrs | Oil | 66.7% |

TABLE 1-continued

| Compound | Aryl-amine | Reaction Time | M.P. ° C. | Yield |
|---|---|---|---|---|
| TQ7 | (3,4-dimethoxybenzyl) | 24 hrs | Oil | 61.1% |
| TQ8 | | 5 days | 68-72 | 52.3% |

The results of the elemental and spectral analyses of the synthesized thymoquinone derivatives (TQ1-TQ8) are provided below:

EXAMPLE 1

5-Isopropyl-2-methyl-3-((2-morpholinoethyl) amino)-1,4-benzoquinone (TQ1)

The compound of example 1 (TQ1) was separated by silica gel column chromatography using hexane/ethyl acetate 6:4 as a mobile phase.

$R_f$ for the product is 0.235. It was obtained as dark violet crystals after 48 hrs, yield 68.3%, mp 92-95° C.; IR (KBr, ν cm$^{-1}$): 3306 (N—H), 1650 and 1615 (C=O), 1118 (C—O—C); $^1$H NMR (400 MHz, DMSO-d$_6$) δ ppm 1.03 (6 H, d, J=6.8 Hz) 1.93 (3 H, s) 2.36 (4 H, t, J=4.6 Hz) 2.47 (2 H, t, J=6.8 Hz) 2.85 (1 H, m) 3.50-3.56 (6 H, m) 6.27 (1 H, t, J=5.6 Hz) 6.33 (1 H, s); $^{13}$C NMR (400 MHz, DMSO-d$_6$) δ ppm 10.07, 21.56, 26.44, 41.24, 53.32, 57.83, 66.7, 107.81, 132.7, 145.58, 149.79, 184.73, 185.69. EI-MS: m/z 292.2, 0.9% (M$^+$), 232.1, 23.1%, 206.1, 61.1%, 149.0, 67.6%, 100, 100%. Elemental analysis (C$_{16}$H$_{24}$N$_2$O$_3$), calculated: C, 65.73%; H, 8.27%; N, 9.58%. Found: C, 66.57%; H, 8.72%; N, 8.59%.

EXAMPLE 2

5-Isopropyl-2-methyl-3-(4-trifluoromethylbenzy-lamino)-1,4-benzoquinone (TQ2)

The compound of example 2 (TQ2) was purified by silica gel column chromatography using hexane/ethyl acetate 8:2 as a mobile phase.

$R_f$ for the product is 0.485. It was obtained as dark red crystals after 64 hrs, yield 50.1%, mp 110.5-112° C.; IR (KBr, ν cm$^{-1}$): 3313 (N—H), 1666 and 1649 (C=O); $^1$H NMR (400 MHz, DMSO-d$_6$) δ ppm 1.00 (6 H, d, J=6.8 Hz) 1.77 (3 H, s) 2.84 (1 H, m) 4.72 (2 H, d, J=7.6 Hz) 6.31 (1 H, s) 7.08 (1 H, t, J=7.4 Hz) 7.44 (2 H, d, J=8.0 Hz) 7.68 (2 H, d, J=8.4 Hz); $^{13}$C NMR (400 MHz, DMSO-d$_6$) δ ppm 9.81, 21.44 26.41, 47.24, 108.24, 125.78, 125.81, 127.47, 127.99, 132.19, 145.36, 146.22, 150.07, 184.78, 185.69. EI-MS: m/z 337.3, 94.4% (M$^+$), 322.2, 24.1%, 192.1, 100%, 178.1, 46.3%, 159.0, 46.3%. Elemental analysis (C$_{18}$H$_{18}$F$_3$NO$_2$), calculated: C, 64.09%; H, 5.38%; N, 4.15%, Found: C, 65.15%; H, 5.34%; N, 3.76%.

EXAMPLE 3

5-Isopropyl-2-methyl-3-(4-fluorobenzylamino)-1,4-benzoquinone (TQ3)

The compound of example 3 (TQ3) was separated by silica gel column chromatography using hexane/ethyl acetate 7:3 as a mobile phase.

$R_f$ for the product is 0.530. It was obtained as dark red crystals after 72 hrs, yield 45.2%, mp 80-82.5° C.; IR (KBr, cm$^{-1}$): 3315 (N—H), 2967, 1667 and 1650 (C=O); $^1$H NMR (400 MHz, DMSO-d$_6$) δ ppm 1.00 (6 H, d, J=6.4 Hz) 1.79 (3 H, s) 2.84 (1 H, m) 4.61 (2 H, d, J=6.4 Hz) 6.30 (1 H, s) 6.95 (1 H, t, J=8.0 Hz) 7.13 (2 H, t, J=8.0 Hz) 7.25 (2 H, t, J=8.0 Hz); $^{13}$C NMR (400 MHz, DMSO-d$_6$) δ ppm 9.88, 21.45, 26.42, 46.91, 108.14, 115.55, 115.76, 128.74, 128.82, 132.29, 137.22, 145.35, 150, 160.34, 162.75, 184.81, 185.71. EI-MS: m/z 287.2, 100% (M$^+$), 272.2, 35.2%, 192.1, 46.3%, 178.1, 57.4%, 109.0, 97.2%. Elemental analysis (C$_{17}$H$_{18}$FNO$_2$), calculated C, 71.06%; H, 6.31%; N, 4.87%, Found: C, 72.16%; H, 6.95%; N, 5.67%.

EXAMPLE 4

5-Isopropyl-2-methyl-3-(benzylamino)-1,4-benzoquinone (TQ4)

The compound of example 4 (TQ4) was purified by column chromatography using hexane/ethyl acetate 8:2 as a mobile phase.

$R_f$ for the product is 0.636. It was obtained as dark red crystals after 72 hrs, yield 73.6%, mp mp 83-84.5° C.; IR (KBr, cm$^{-1}$): 3312 (N—H), 2966, 1665 and 1650 (C=O); $^1$H NMR (400 MHz, DMSO-d$_6$) δ ppm 1.00 (6 H, d, J=6.8 Hz) 1.80 (3 H, s) 2.84 (1 H, m) 4.63 (2 H, d, J=7.2 Hz) 6.30 (1 H, s) 6.95 (1 H, t, J=7.0 Hz) 7.19-7.23 (3 H, m) 7.28-7.32 (2 H, m); $^{13}$C NMR (400 MHz, DMSO-d$_6$) δ ppm 9.87, 21.44, 26.42, 47.53, 107.84, 126.74, 127.24, 128.93, 132.37, 141.08, 145.41, 149.91, 184.82, 185.69. EI-MS: m/z 269.2, 100% (M$^+$), 254.2, 30.6%, 192.1, 75.0%, 178.1, 45.4%, 91.0, 81.5%. Elemental analysis (C$_{17}$H$_{19}$NO$_2$): calculated C, 75.81%; H, 7.11%; N, 5.2%. Found: C, 76.95%; H, 7.39%; N, 5.62%.

EXAMPLE 5

5-Isopropyl-2-methyl-3-(3,5-ditrifluoromethylbenzylamino)-1,4-benzoquinone (TQ5)

The compound of example 5 (TQ5) was purified by column chromatography using hexane/ethyl acetate 8:2 as a mobile phase.

$R_f$ for the product is 0.485. It was obtained as dark red crystals after 48 hrs, yield 47.2%, mp 111-114° C.; IR (KBr, cm$^{-1}$): 3319 (N—H), 2974, 1677 and 1649 (C=O); $^1$H NMR (400 MHz, DMSO-d$_6$) δ ppm 1.00 (6 H, d, J=6.8 Hz) 1.77 (3 H, s) 2.84 (1 H, m) 4.76 (2 H, d, J=7.6 Hz) 6.31 (1 H, s) 7.02 (1 H, t, J=7.2 Hz) 7.95 (3 H, s) 7.96 (3 H, s); $^{13}$C NMR (400 MHz, DMSO-d$_6$) δ ppm 9.97, 21.4, 26.41, 47.18, 109.73, 121.04, 122.44, 125.16, 127.9, 130.45, 130.78, 131.85, 145.01, 145.72, 150.38, 184.82, 185.79. EI-MS: m/z 405.2, 0% (M$^+$), 390.2, 75.0%, 321.2, 31.5%, 242.1, 100%, 227.1, 44.4%, 192.1, 36.1%, 178.2, 21.3%, 148.1, 18.4%. Elemental analysis (C$_{19}$H$_{17}$F$_6$NO$_2$): calculated C, 56.3%; H, 4.23%; N, 3.46%. Found: C, 57.05%; H, 4.10%; N, 2.64%.

EXAMPLE 6

5-isopropyl-2-methyl-3-(2-hydroxyethylamino)-1,4-benzoquinone (TQ6)

The compound of example 6 (TQ6) was purified by silica gel column chromatography using hexane/ethyl acetate 9:1 then 7:3 as a mobile phase.

$R_f$ for the product is 0.524. It was obtained as dark violet gum after 36 hrs, yield 66.7%; IR (KBr, cm$^{-1}$): 3408.7 (N—H), 2925, 1665.4, 1649.3 (C=O); $^1$H NMR (400 MHz, CHLOROFORM-d) δ ppm 1.09 (6 H, d, J=6.4 Hz) 2.04 (3 H, s) 2.95 (1 H, m) 3.64 (2 H, t, J=5.0 Hz) 3.82 (2 H, t, J=5.2 Hz) 5.70 (1 H, s) 6.39 (1 H, s); $^{13}$C NMR (400 MHz, CHLOROFORM-d) δ ppm 10.32, 21.31, 26.51, 46.97, 61.92, 109.19, 132.88, 144.70, 149.97, 184.72, 186.89. EI-MS: m/z 223.2, 23.8% (M$^+$), 192.1, 100%, 177.1, 13.8%, 149.1, 11.0%. Elemental analysis (C$_{12}$H$_{17}$NO$_3$): calculated: C, 64.55%; H, 7.67%; N, 6.27%; 0, 21.50%.

EXAMPLE 7

5-isopropyl-2-methyl-3-(3,4-dimethoxybenzylamino)-1,4-benzoquinone (TQ7)

The compound of example 7 (TQ7) was purified by silica gel column chromatography using hexane/ethyl acetate 1:1 as a mobile phase.

$R_f$ for the product is 0.524. It was obtained as dark red gum after 24 hrs, yield 61.1%; IR (KBr, cm$^{-1}$): 3394 (N—H), 2926, 1649 (C=O); $^1$H NMR (400 MHz, CHLOROFORM-d) δ ppm 1.08 (6 H, d, J=6.8 Hz) 2.05 (3 H, s) 2.94 (1 H, m) 3.85 (6 H, s) 4.57 (2 H, d, J=3.6 Hz) 5.64 (1 H, s) 6.39 (1 H, s) 6.72-6.87 (3 H, m); $^{13}$C NMR (400 MHz, Chloroform-d) δ ppm 10.27, 21.30, 26.51, 49.13, 55.88, 109.21, 110.31, 111.35, 119.48, 131.07, 132.96, 144.37, 149.28, 149.85, 184.49, 186.91. EI-MS: m/z 329.2, 0% (M$^+$), 314.2, 286.1, 192, 178.1, 137.1. Elemental analysis (C$_{19}$H$_{23}$NO$_4$): calculated: C, 69.28%; H, 7.04%; N, 4.25%; 0, 19.43%.

EXAMPLE 8

(3-amino-5-isopropyl-2-methyl-1,4-benzoquinone (TQ8)

The compound of example 8 (TQ8) was obtained as dark violet crystals, yield 52.3%, mp 68-72° C.; IR (KBr, cm$^{-1}$): 3461 and 3328 (N—H$_2$), 2966, 1673 and 1649 (C=O); $^1$H NMR (400 MHz, DMSO-d$_6$) δ ppm 1.02 (6 H, d, J=7.2 Hz) 1.69 (3 H, s) 2.84 (1 H, m) 6.25 (1 H, d, J=1.2 Hz) 6.43 (2 H, s, exchangeable with D$_2$O); $^{13}$C NMR (400 MHz, DMSO-d$_6$) δ ppm 8.97, 21.47, 26.3, 106.99, 132.37, 145.49, 149.54, 183.99, 185.41. EI-MS: m/z 179.2, 100% (M$^+$), 164.1, 36.7%, 136.1, 62.4%, 108.1, 38.5%. Elemental analysis (C$_{10}$H$_{13}$NO$_2$): calculated C, 67.02%; H, 7.31%; N, 7.82%. Found: C, 66.65%; H, 7.15%; N, 7.81%.

Effects of Synthesized Compounds on Cancerous Cell Lines

Cellular Viability

Human lung cancer cells A549, human breast cancer cells MDA-MB-231 and colorectal cancer cells HT29, were used to test the antiproliferative activity of the synthesised compounds. Human lung cancer cells A549 were maintained in RPMI 1640 medium (Hyclone Laboratories, USA), human breast cancer cells MDA-MB-231 and colorectal cancer cells HT29 were maintained in DMEM medium (Hyclone Laboratories, USA). All media was supplemented with antibiotics (penicillin 50 U/ml; streptomycin 50 ug/m1) (Hyclone Laboratories, USA).

Cells were seeded at a density of 5,000 cells/well into 96-well plates. After 24 h, cells were treated for 24 and 48 h with different concentrations of compounds TQ1-5 and 8 (5-100 µM), in triplicate. Control cultures were treated with 0.1% DMSO. The effect of the compounds TQ1-8 on cell viability was determined using the CellTiter-Glo Luminescent Cell Viability assay (Promega Corporation, Madison, USA), based on quantification of ATP, which signals the presence of metabolically active cells. The luminescent signal was measured using the GLOMAX Luminometer system. Data were presented as proportional viability (%) by comparing the treated group with the untreated cells, the viability of which is assumed to be 100%.

The anticancer effects of the compounds were tested on human lung cancer cell line (A549), breast cancer cell (MDA-MB-231) and colorectal cancer cell lines (HT29) using cell viability assay.

Figure 1B:
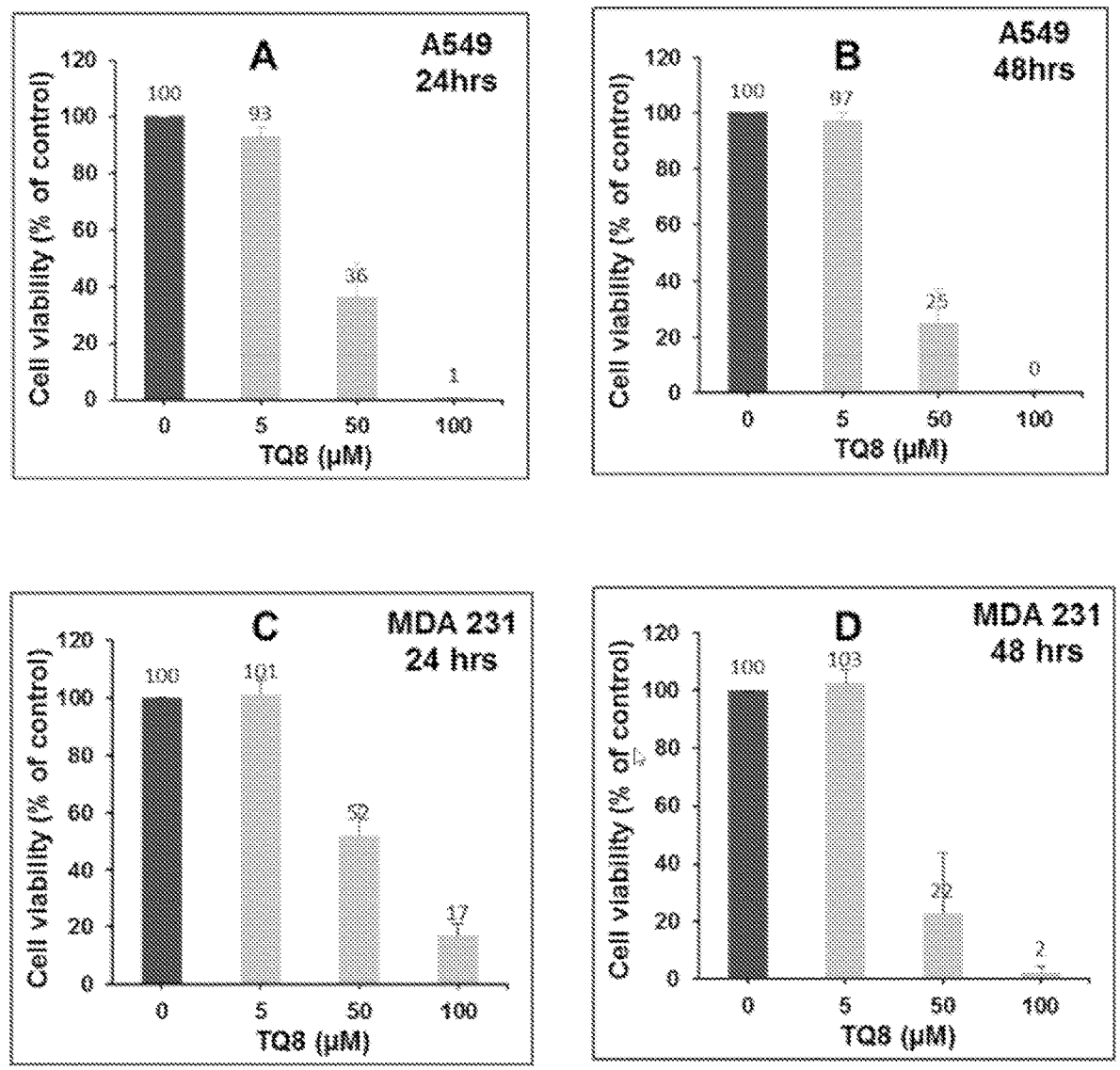
Figure 1B:
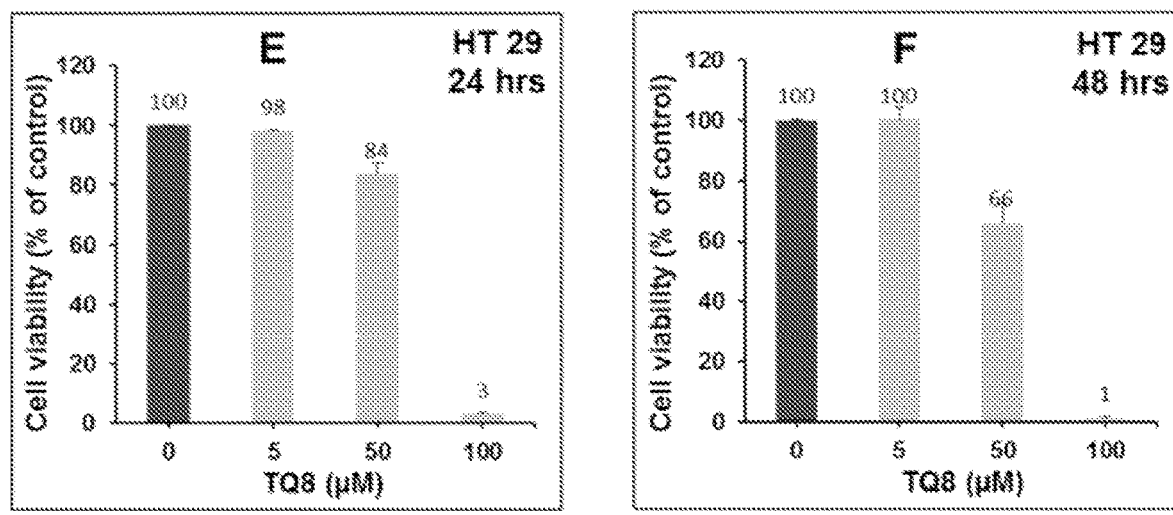

FIGS. 1A and 1B show the effects of compounds TQ 1-5 and 8 on the cell viabilities of human lung cancer cell line, A549, using 5, 50 and 100 µM concentrations. Values are recorded relative to the control sample (DMSO).

Decreases in cellular viability of cancerous cells are observed with increasing drug concentration and time of exposure (24-48 hours). The six compounds at 100 µM concentrations gave steady decreases in cell viability after 24 hours by 15, 32, 29, 17, 33 and 99% relative to the control (DMSO), respectively. After 48 hours exposure, further decreases of 33, 57, 64, 58, 48 and 100% in cell viability were observed.

These results indicate a toxic effect against lung cancer cells for compounds TQ1-5 and TQ8. TQ8 had the highest toxic effect of the derivatives tested with cell viability close to zero relative to the control after 24 hours. Compound TQ8 was further tested on breast and colorectal cancer cell lines. All experiments were repeated at least three times.

FIG. 1B shows the effects of compound TQ8 on the cellular viability of MDA-MB-231 and HT29 cells over 24 and 48 hours using 5-100 µM concentrations. A concentration and time-dependent decrease in cell viability was observed. The losses in cell viability were 83% and 97% using 24 hours exposure at 100 µM concentrations. These losses increased to 98% and 99% after 48 hours exposure for MDA-MB-231 and HT29 cell lines, respectively.

Compound TQ8 showed the best potency among the eight synthesized thymoquinone derivatives against examined cancerous cell lines. A complete suppression of cell viability was observed at 48 hours using 100 µM. The relative cytotoxic effect of compound TQ8 on tested cancer cell lines was found in the following order A549>MDA-MB-231>HT29.

An IC50 gives a good estimate of the cytotoxic potency of different drugs against cancer cells. The IC50s (concentration produces 50% inhibition in cells viabilities) for compounds TQ1-5 and TQ8 at 24 hours are shown in Table 2.

The results ranged from 35.01-105.05 µM for tested thymoquinone derivative compounds against A549 cell line. TQ8 gave IC50s of 35.01, 45.14 and 55.81 µM against A549, MDA-MB-231 and HT29 cells, respectively. These results indicate good IC-50 values against the tested cells lines.

These results also indicate that compound TQ8 is 200% potent compared to the parent TQ molecule whose IC50 has been reported as 78.34 µM against A549 cells.

TABLE 2

IC50s of thymoquinone derivatives

| Compound | IC 50 (µM) | | |
|---|---|---|---|
| | A 549 | MDA 231 | HT29 |
| TQ | 78.34 | — | — |
| TQ1 | 74.32 | — | — |
| TQ2 | 84.29 | — | — |
| TQ3 | 83.19 | — | — |
| TQ4 | 88.65 | — | — |
| TQ5 | 105.05 | — | — |
| TQ8 | 35.01 | 45.14 | 55.81 |

The cytotoxic effects for the compounds seen against the cancer cells indicate that the compounds could be suitable in the use of the treatment of cancers.

The compounds of the invention, TQ1-8, may be particularly good in in vivo models.

Interaction of G-Quadruplex DNA with TQ Ligands

Several mechanisms have been suggested for the anti-tumour effects of thymoquinone compounds. Stabilising the formation of G-quadruplex DNA structures with small molecules has been found to inhibit the telomerase enzyme found in active cancer cells, and has been seen as an effective approach for developing anticancer molecules. Therefore the thymoquinone derivatives were tested for their binding affinity and selectivity towards G-quadruplex DNA.

DNA solutions for use in the following assays were prepared as described below:

Calf Thymus DNA (Ct-DNA)

A 1000 µg/ml calf thymus ds-DNA was prepared by dissolving 10 mg of DNA (Sigma-Aldrich) into 10 ml Tris-KCl buffer, pH 7.4, without sonication or stirring. The solution was gently inverted overnight at 4° C. to completely solubilize the DNA and prevent shearing of the large genomic DNA. Resultant ct-DNA solutions are stable at 4° C. for several months.

Single Stranded DNA

Purchased synthetic nucleic acids primers (AlphaDNA, Canada) with human telomere sequence; 5'-AGGGT-TAGGGTTAGGGTTAGGG-3' (SEQ ID NO:1), its fluorescein labelled 5' primer 5'-Fl-AGGGTTAGGGTTAGGGT-TAGGG-3' (SEQ ID NO: 2) or its complementary strand 3'-TCCCAATCCCAATCCCAATCCC-5' (SEQ ID No: 3) were reconstituted by centrifugation for 10 min at 7000 rpm to collect the DNA into the vials' bottoms. A 2.00 ml Tris-KCl buffer, pH 7.4, was added to each vial, left 2 min for rehydration then vortexed for 30 seconds. Reconstituted primers were kept overnight at 4° C. before use. Stability of reconstituted primers is more than 6 months.

G-Quadruplex DNA

A 2 ml of the stock single stranded DNA; 5'-AGGGT-TAGGGTTAGGGTTAGGG-3' (SEQ ID NO: 1) was gently heated up to 95° C., incubated for 10 minutes and then left to cool to room temperature. Resultant solution was kept in fridge at 4° C. overnight.

Hybridization of Telomeric DNA

A $10^{-4}$ M telomeric dsDNA was prepared by mixing equimolar amounts of 5'-AGGGTTAGGGTTAGGGT-TAGGG-3' (SEQ ID No: 1) (268.80 µL of $7.44 \times 10^{-4}$ M) and complementary strand 3'-TCCCAATCCCAATCC-CAATCCC-5'(SEQ ID NO: 3) (738.0 µL of $2.71 \times 10^{-4}$ M). The solution was made up to 2 ml using KCl-Tris-Cl buffer, pH 7.4, vortexed for 15 seconds, incubated at 95° C. for 10 min and left to cool to room temperature. Resultant hybridized dsDNA was kept at 4° C. until use.

Concentrations of reconstituted stock DNA solutions were determined by diluting 10 µl of each solution to 1 ml using KCl buffer, pH 7.4. Solutions were vortexed for 15 seconds and its absorbance were measured at 260 and 280 nm. Concentrations were calculated using C (µg/ml)=A260× weight per OD×dilution factor, where A is the absorbance at 260 nm. The purity of oligonucleotides was estimated based on the ratio A260/A280. Ratios ≥1.8 were considered enough to indicate high purity. Since G-quadruplex DNA is formed by folding up from single strands, its concentration was similar to that of its single stranded DNA.

TQ Stability

The stability of the thymoquinone derivatives in Tris-KCl buffer, pH 7.4 at room temperature were investigated using UV-Vis spectrophotometry. Solutions were found stable and no change in absorbance for up to 12 hrs. However, decay in absorbance was observed when solutions kept for longer times. Therefore, freshly prepared solutions were used throughout.

To confirm an interaction between the thymoquinone derivatives and G-quadruplex DNA, this interaction was studied using fluorescence, fluorescence quenching and circular dichroism spectroscopies Fluorescence Titration To 3 ml of $5\times10^{-5}$ M of each of compounds TQ1-8 in Tris-KCl-buffer, pH 7.4, successive portions of G-quadruplex DNA ($1.44\times10^{-4}$ M) were added. After each addition, the TQ solution was stirred for 20 seconds, incubated for 3 min and its emission was scanned in the range 300-600 nm using excitation λmax of 280 nm and slit width of 10.00 nm. Titration stopped when no change in fluorescence intensity was observed.

Figure 2:
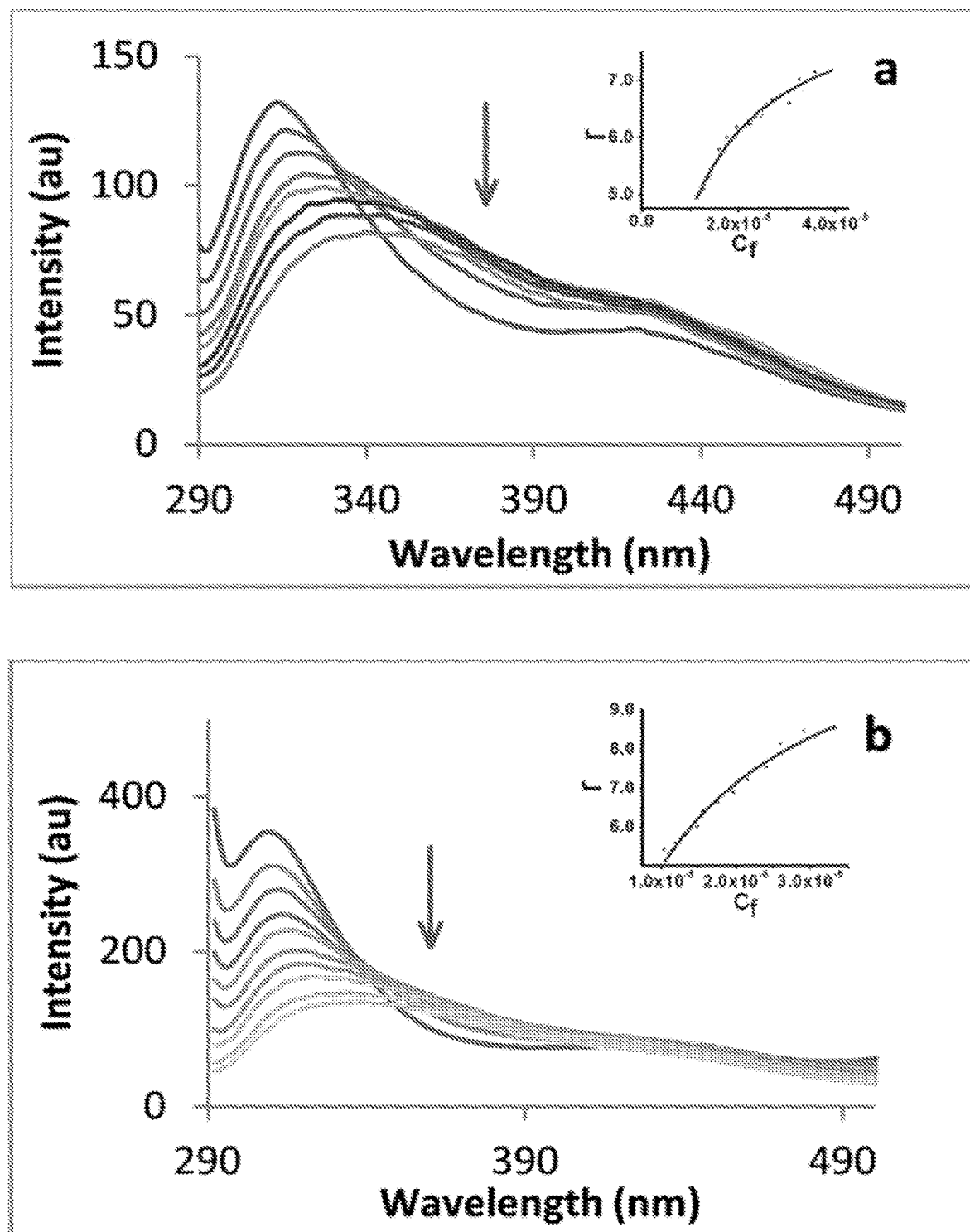
Figure 2:
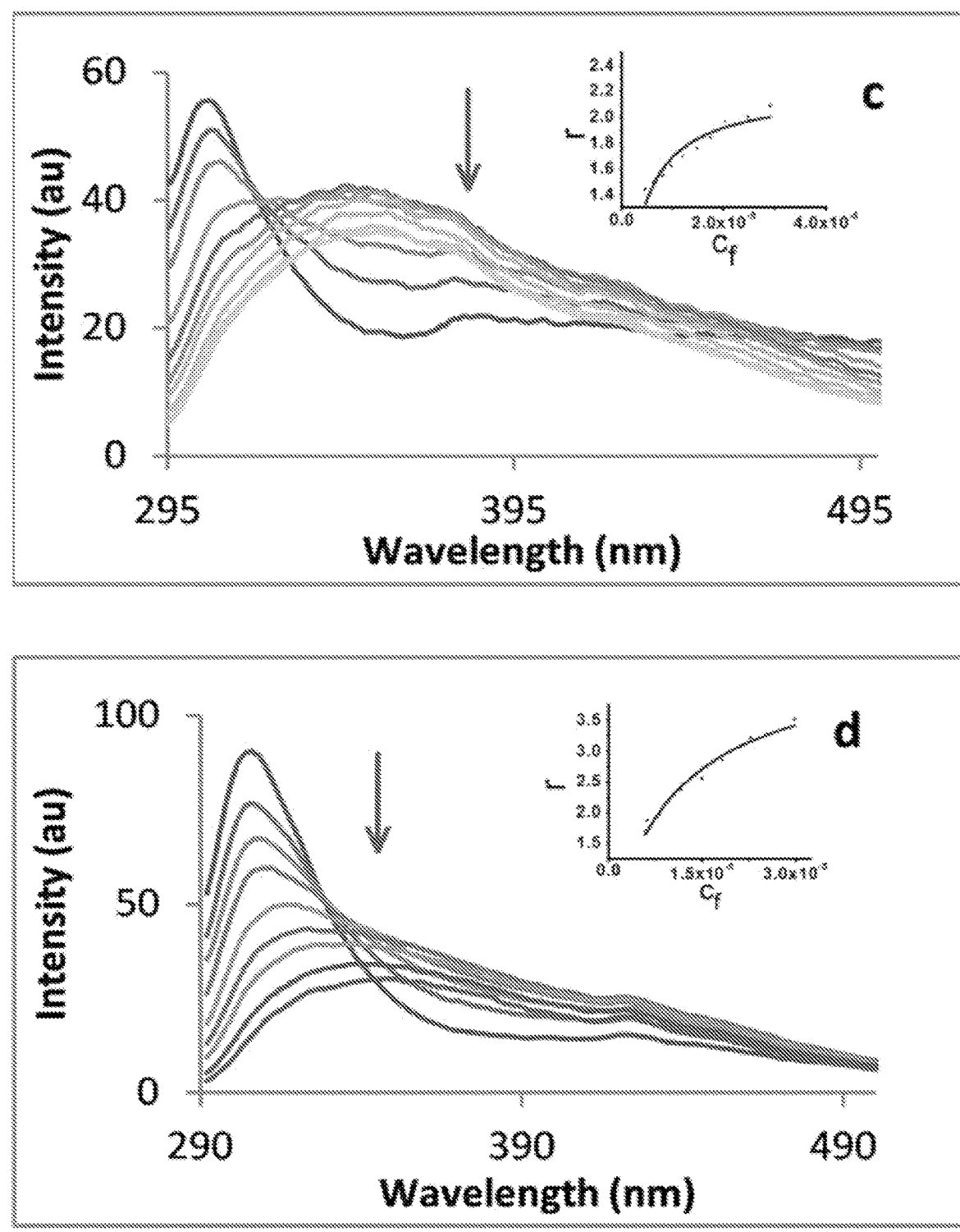
Figure 2:
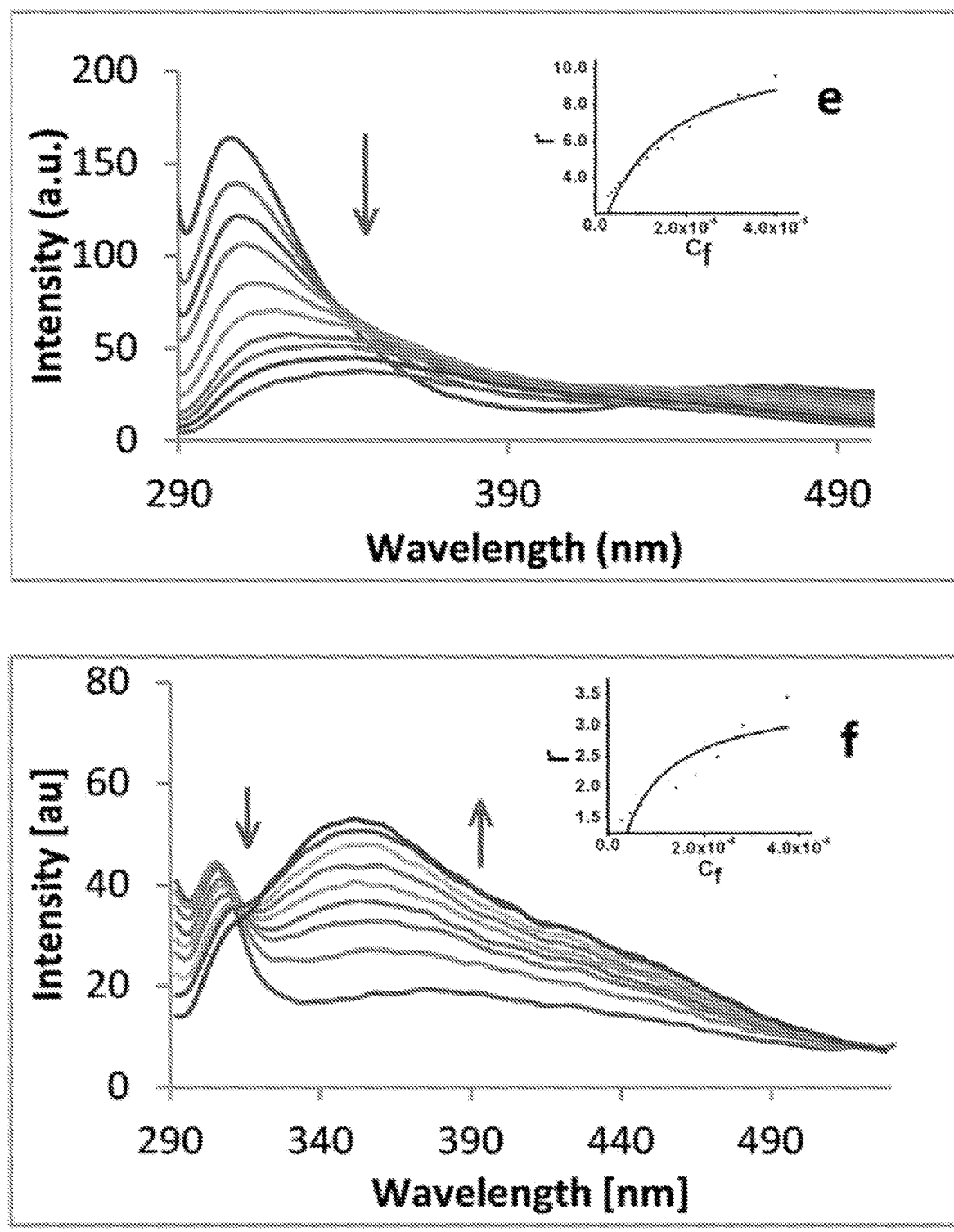
Figure 2:
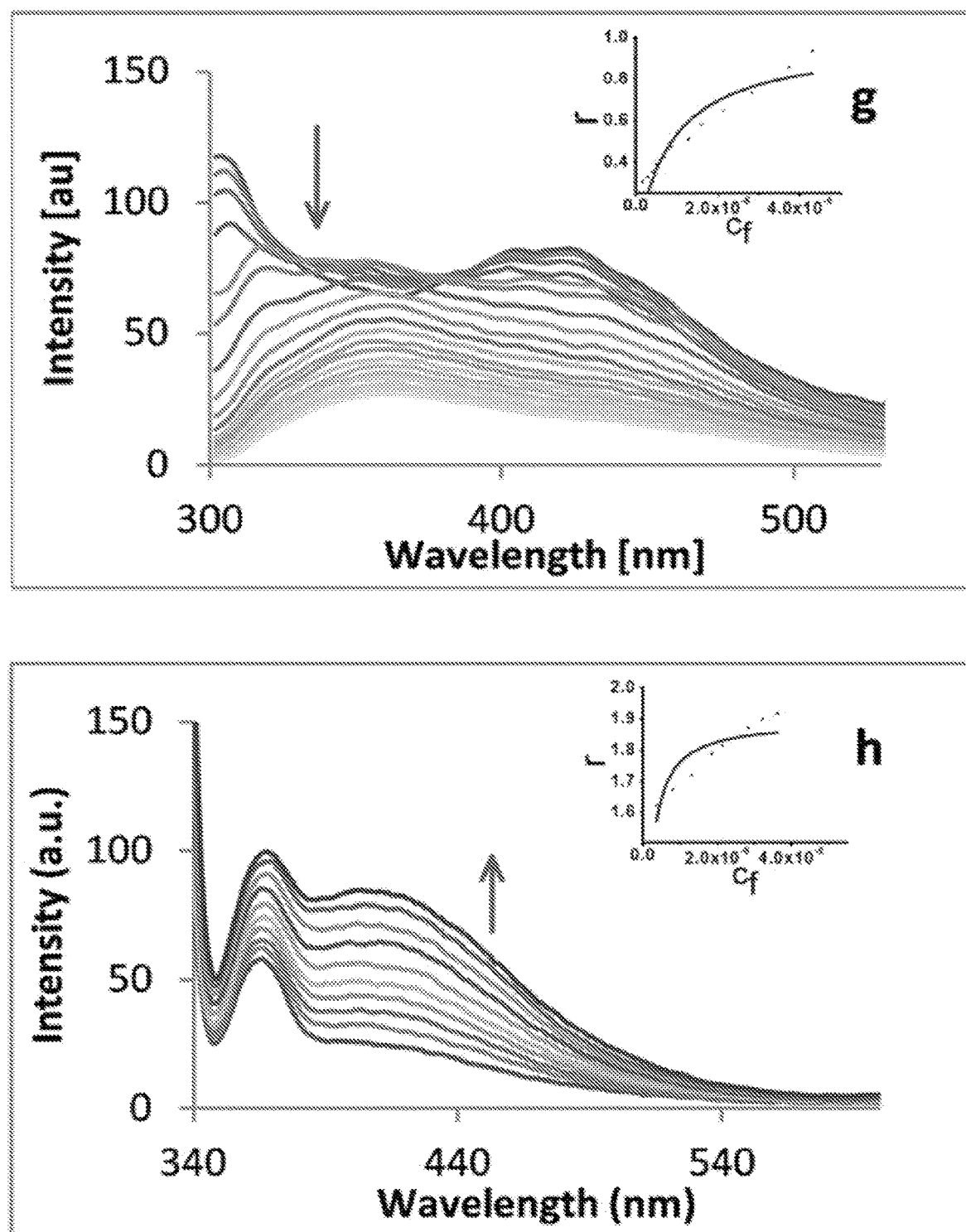

The results are shown in FIG. 2. Fluorescence titrations of compounds TQs 1, 2, 4, 5 and 7 with G-quadruplex DNA showed decrease in fluorescence intensity and red shifts by 24, 14, 30, 25 and 41 nm (FIGS. 2a, 2b, 2d, 2e and 2g). Compounds TQ3 and TQ6 showed a hypochromicity and red shifts by 4 nm and the appearance of a new peak at 353.7 and 350 nm respectively (FIGS. 2c and 2f). Compound TQ6 showed an isosbestic point at 315 nm. Compound TQ8 showed an increase in fluorescence intensity with slight red shift (FIG. 2h). These changes in fluorescence spectra of TQs during titration indicated the binding of TQs with G-quadruplex DNA. The isosbestic point indicates an equilibrium process during binding interaction.

Quenching Assay of Fluorescein Labelled G-Quadruplex

Additional confirmation for TQ-G-quadruplex interactions was obtained through fluorescence quenching titration. The following assay was used to confirm binding interactions of TQ derivatives and their selectivity towards human telomeric G-quadruplex.

To 3 ml of $1\times10^{-7}$ M fluorescein labelled G-quadruplex (5'-Fl-AGGGTTAGGGTTAGGGTTAGGG-3' (SEQ ID NO: 2), successive portions of each of the compounds TQs 1-8 ($10^{-4}$ M) in Tris-KCl buffer, pH 7.4, were added. After each addition, the solution was stirred for 20 seconds, incubated for 3 minutes and scanned for its emission spectra at the Fl-G-quadruplex emission λmax of 518 nm and excitation λmax of 494 nm.

Fluorescence intensity of Fl-G-quadruplex is quenched when a molecule binds it near the fluorescence labelling flag molecule.

Figure 3:
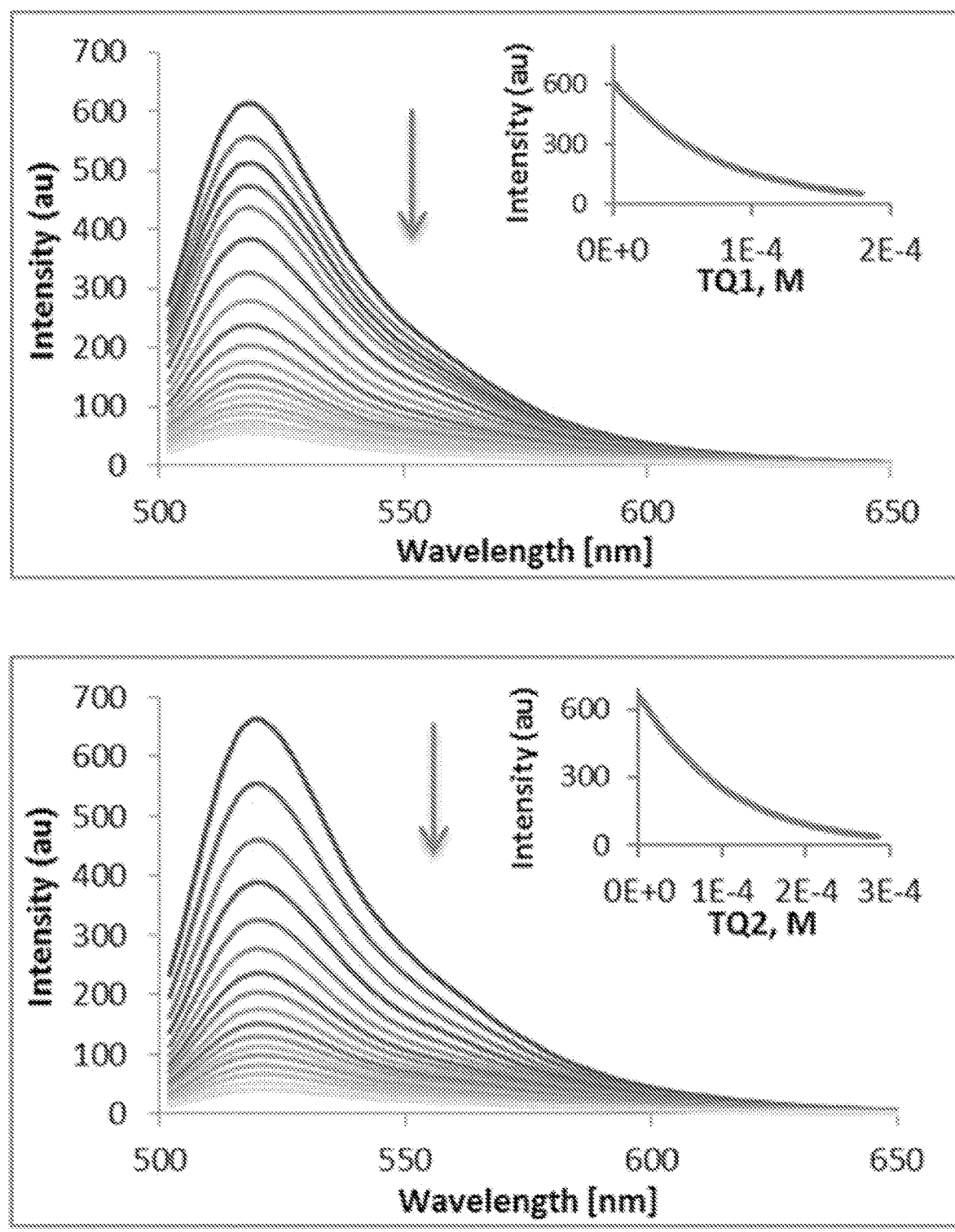
FIG. 3 shows the fluorescence spectra of 5'-Flu-G-quadruplex (2×10−6 M) with compounds TQ1-8. 5'-Fl-G-quadruplex was excited at 494 nm and emitted at 518 nm.
Figure 3:
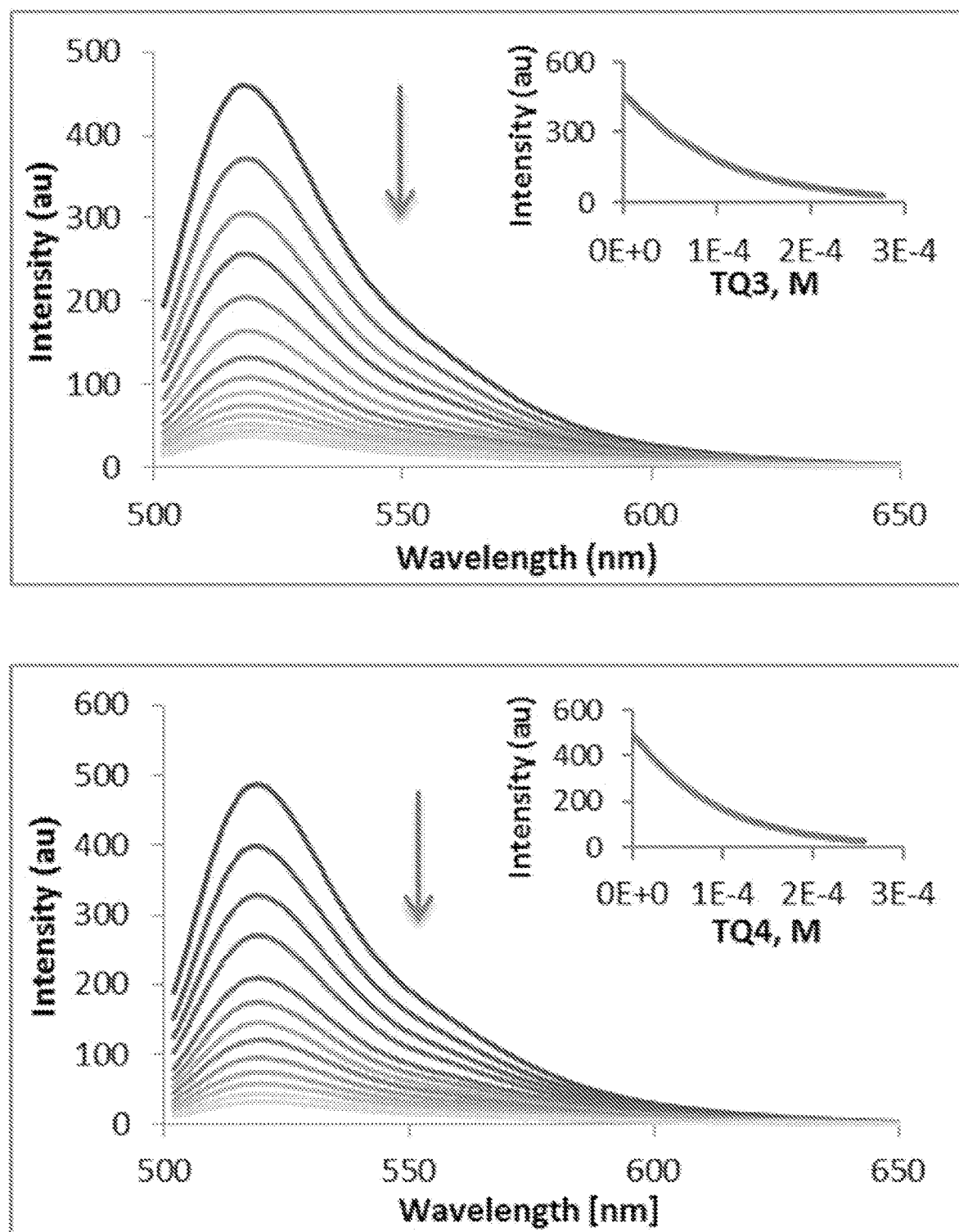
Figure 3:
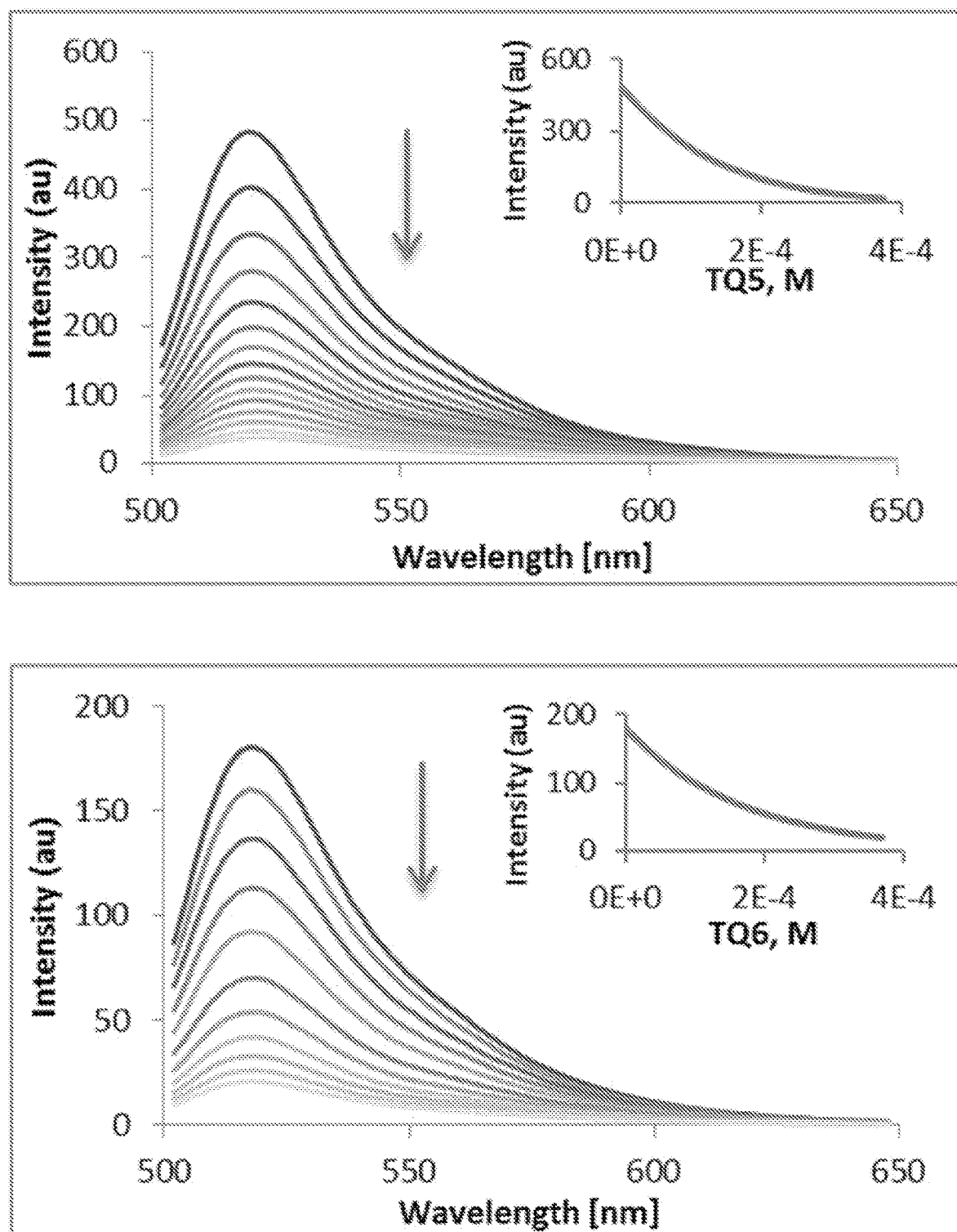
Figure 3:
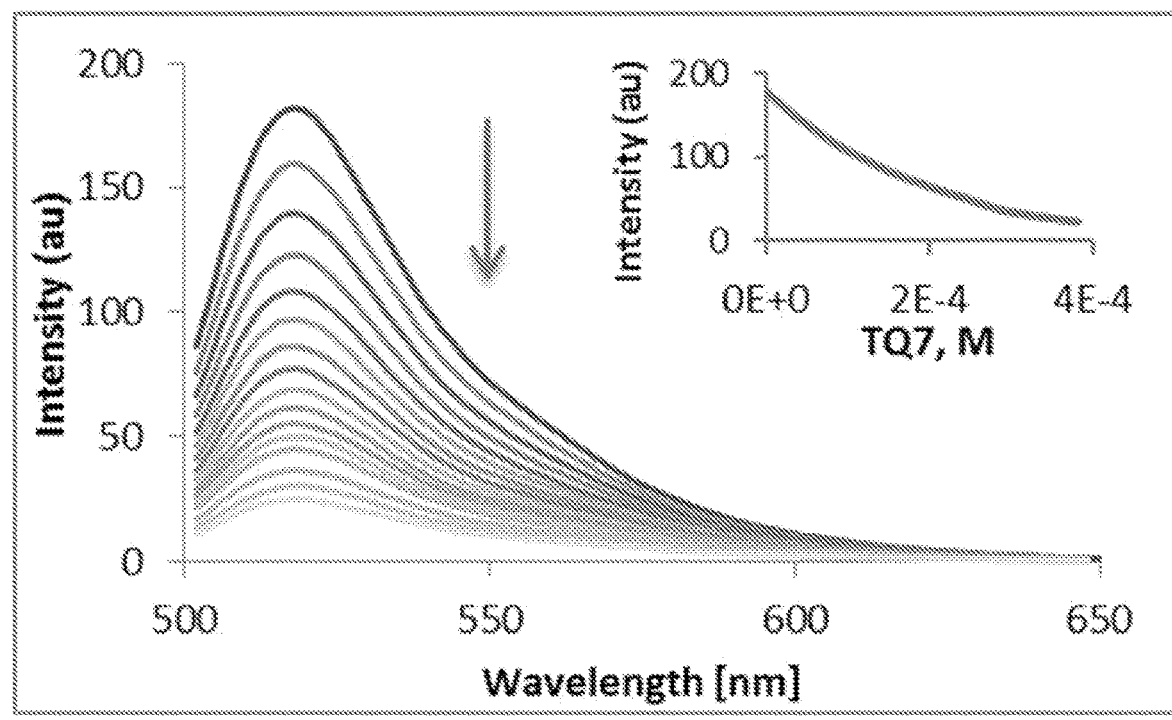
Figure 3:
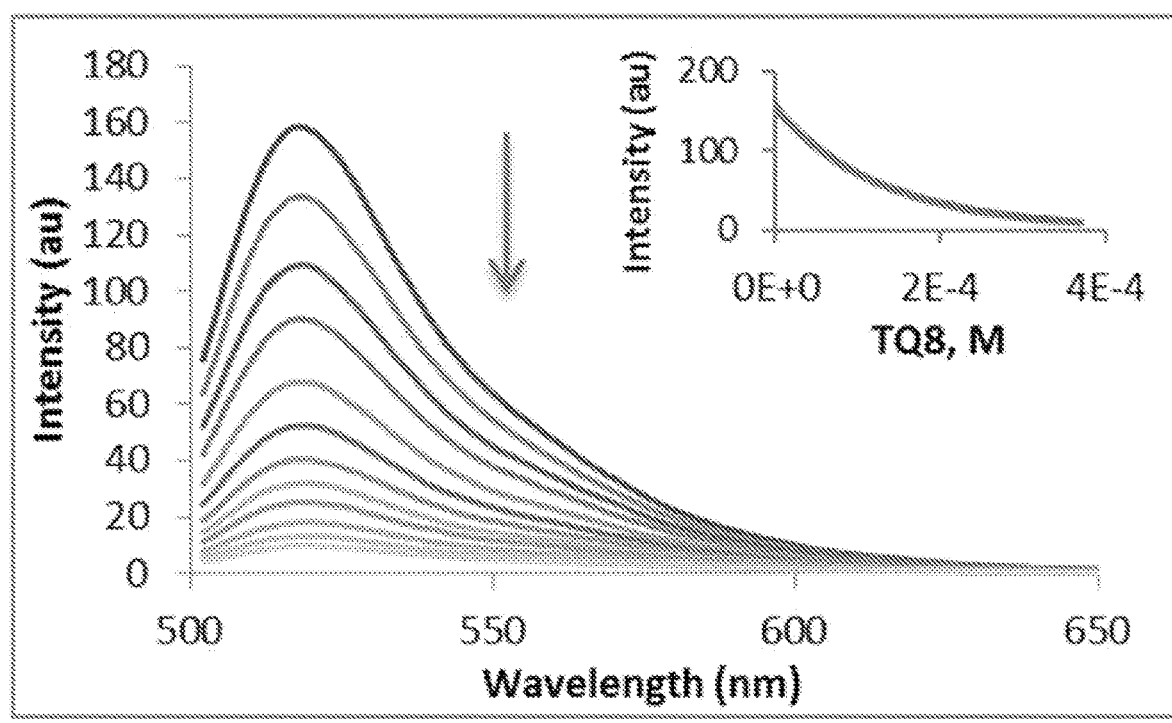

The changes in fluorescence emission of 5'-fluorescein-labelled G-quadruplex DNA at 518 nm using 494 nm as the maximum wavelength of excitation are shown in FIG. 3. Fluorescence of 5'-fluorescein-labelled -quadruplex DNA showed a decrease in fluorescence intensity with successive addition of the thymoquinone derivative compounds. Quenching of 5'-fluorescein-labelled G-quadruplex is attributed to binding of the compounds in fluorescein proximity on Fl-G-quadruplex DNA.

Circular Dichroism Titration

CD spectroscopy was used to follow conformational change of G-quadruplex DNA upon interaction with the thymoquinone derivatives. To 1 ml G-quadruplex DNA ($4\times10^{-6}$ M) in Tris-KCL buffer, pH 7.4, successive amounts of each of the compounds TQ 1-8 ($10^{-4}$ M) were added in ratios [drug]/[G-quadruplex] in the range of 0.2-15. After each addition, the solution was well shaken, incubated for 3 minutes at room temperature and scanned in the range 200-400 nm with 50 nm/min, band width 1 nm and 3 accumulations. Samples' CD were subtracted from the blank and then base line corrected. Changes in CD bands at 293 nm were recorded versus drugs' concentrations.

Interaction between the thymoquinone derivatives and G-quadruplex DNA was also tested by CD titrations. Change in CD intensity during titration has been used to estimate the binding mode between the ligand and DNA. A decrease in CD intensity during DNA titration with ligand has been correlated with an intercalation binding mode while an increase in intensity has been correlated with groove binding mode. Therefore, gradual decrease in CD intensity in the measurements may indicate an interaction mode between the derivative compounds and G-quadruplex.

Figure 4:
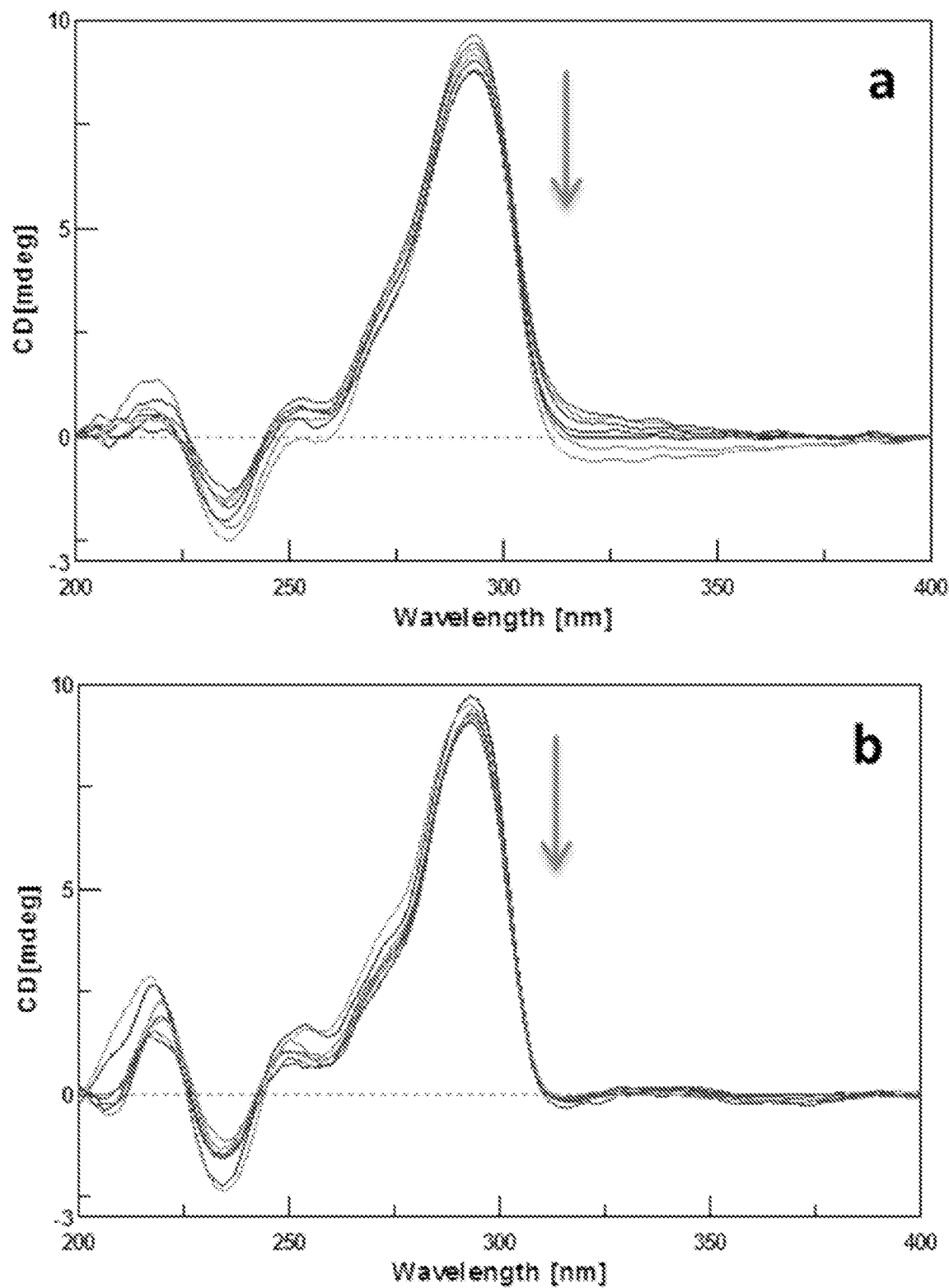
FIG. 4 shows the CD spectra of G-quadruplex (4×10−6 M) with compounds TQ1-8 (a-h respectively).
Figure 4:
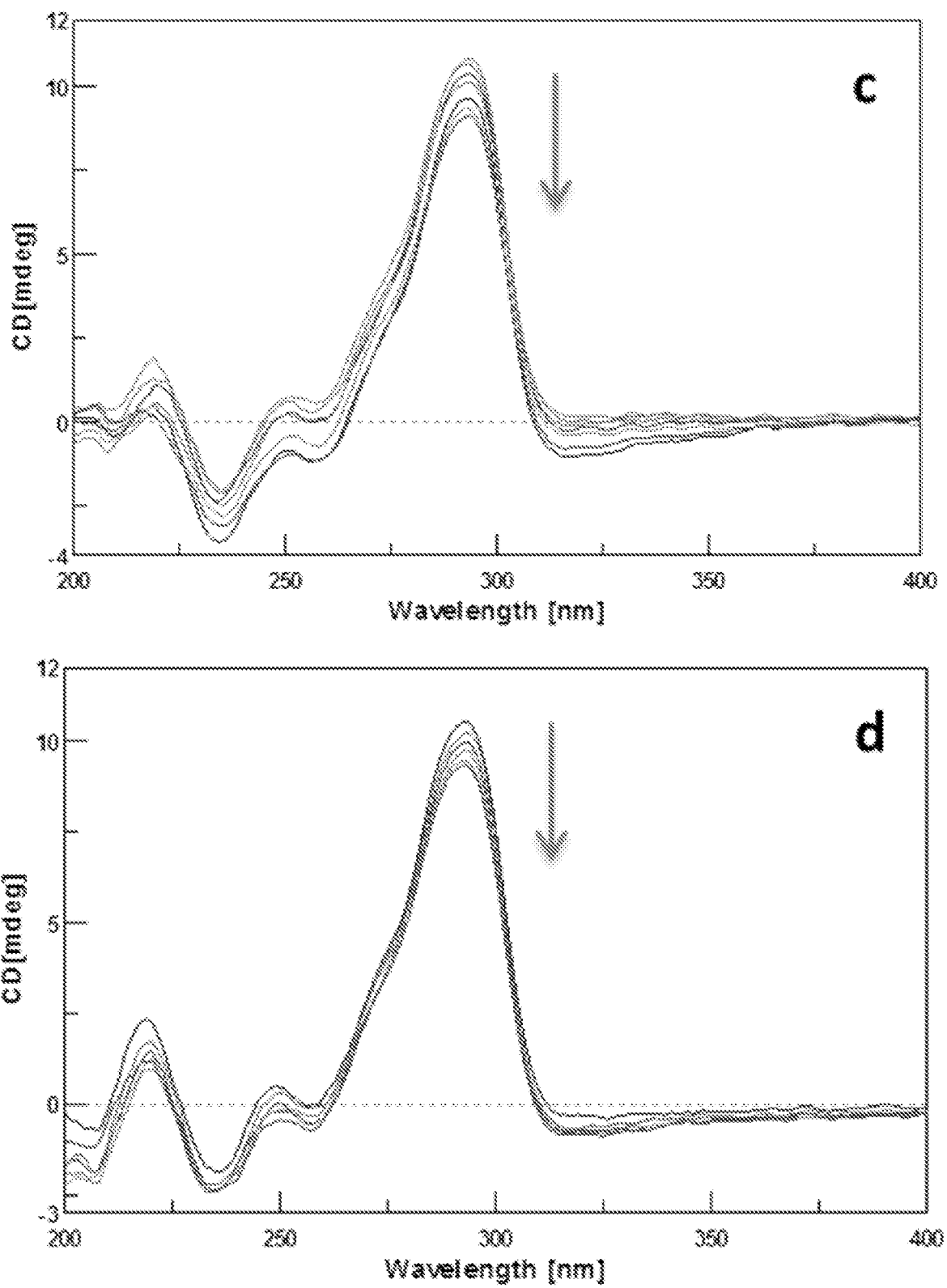
Figure 4:
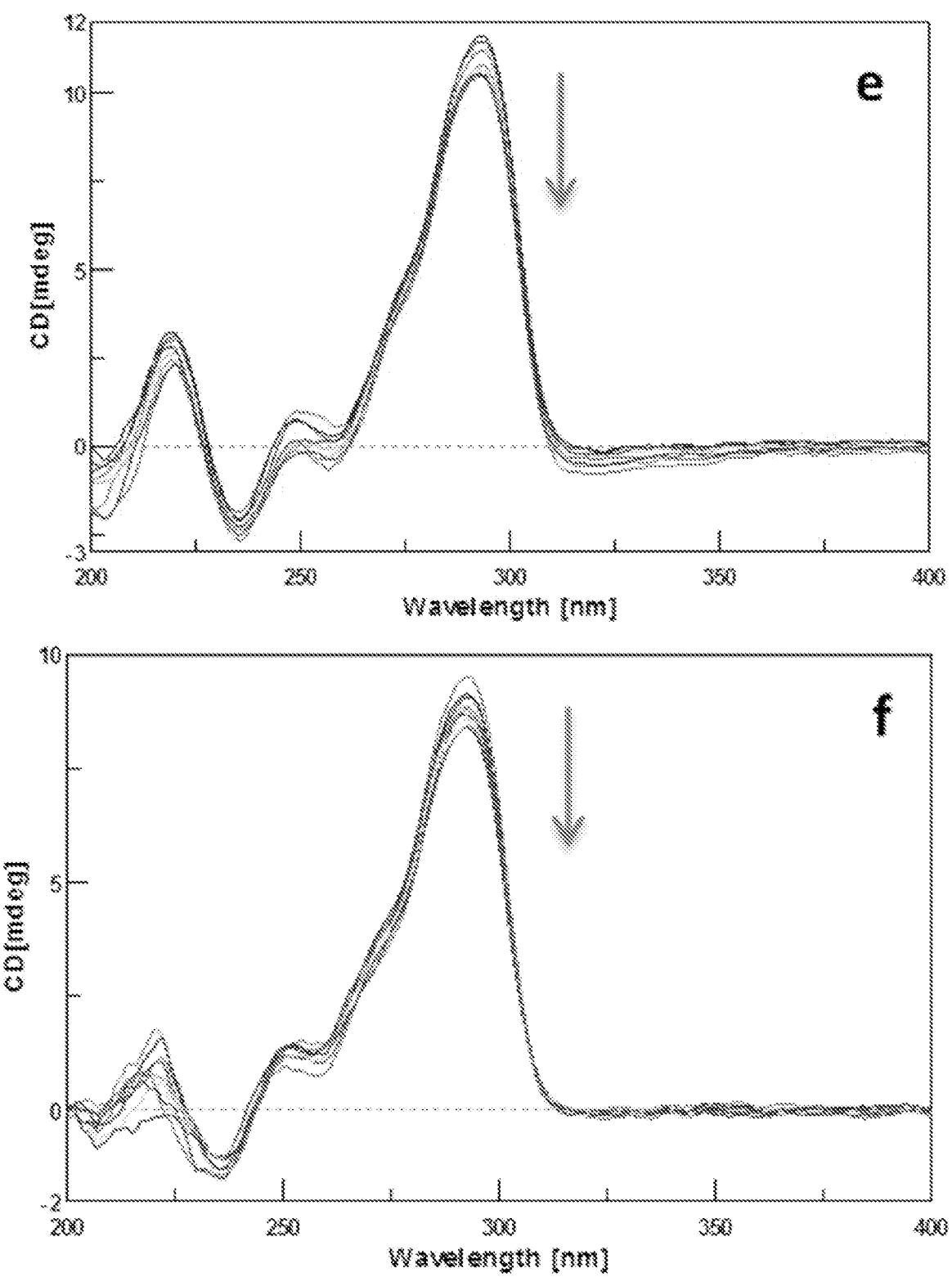
Figure 4:
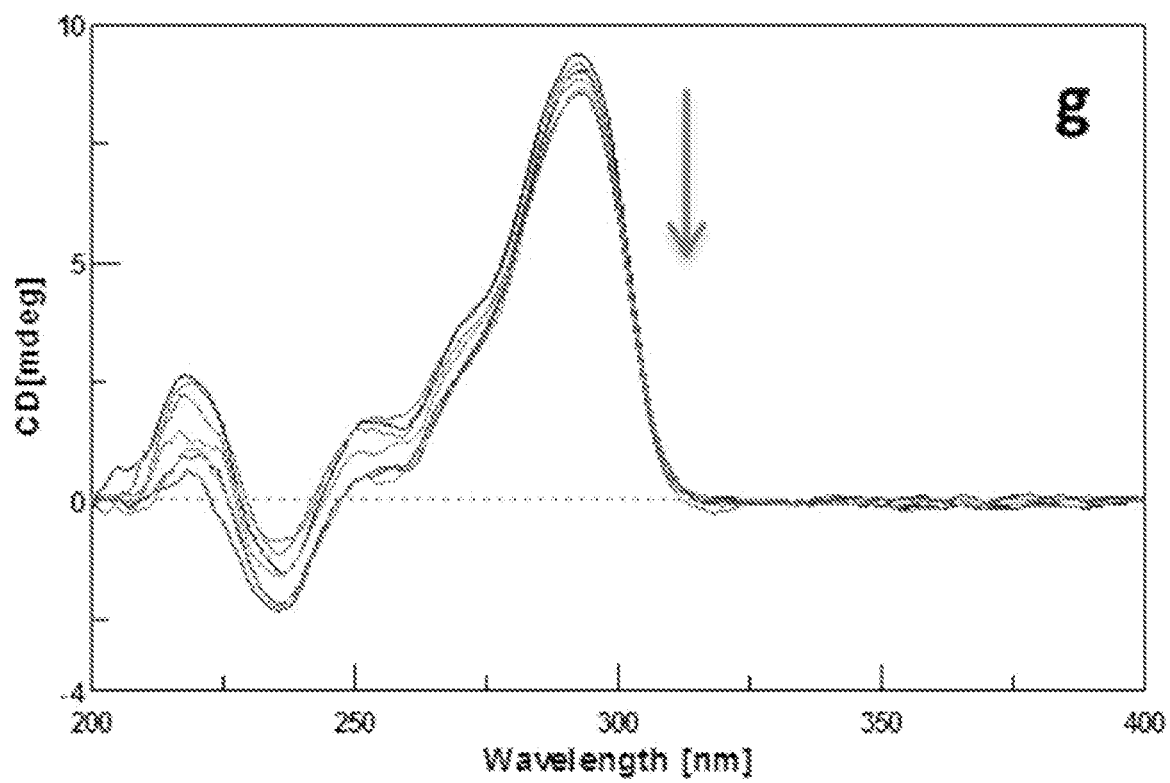
Figure 4:
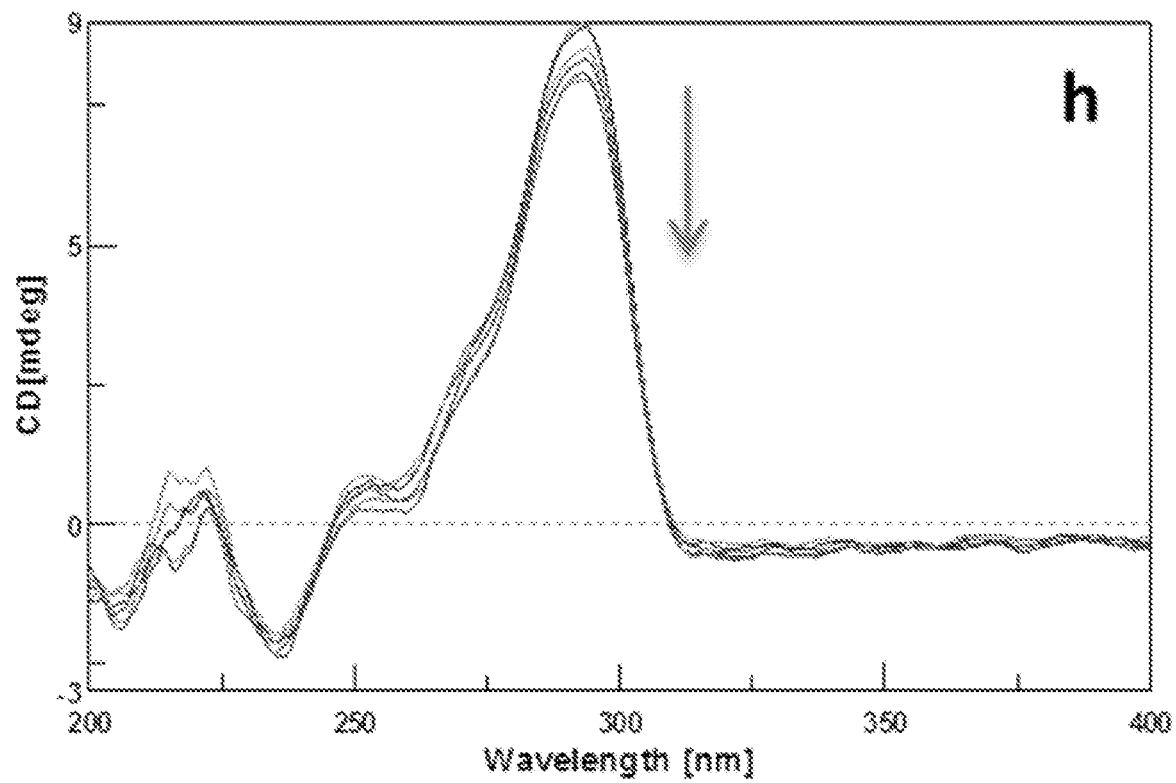

FIG. 4 shows the CD titration spectra of G-quadruplex DNA with compounds TQ1-TQ8 (4a-h). Decreases in CD intensity, without changes in bands positions or shapes indicated a face π-π stacking intercalation process without conformational change in G-quadruplex during titration.

Melting Temperature Curves

In order to determine the stability of DNA upon complexation with ligand and its binding affinity, melting temperatures were determined.

Melting temperature curves for G-quadruplex and their TQs adducts were constructed using CD spectral measurements.

A 1 ml telomeric G-quadruplex ($3.93\times10^{-6}$ M) in Tris-KCl-buffer pH 7.4, was heated in 1-5° C. increments in the range 25-95° C. using 5 minutes incubation time intervals. CD spectra were recorded in the range 200-400 nm using 50 nm/min, 1 nm band width and 3 accumulations at each point. CD spectra were baseline corrected against blank solution and CD intensities at 293 nm were plotted versus temperature.

Similarly G-quadruplex-TQ1-8 1 mL complex solutions that were $3.93\times10^{-6}$ M of G-quadruplex and $3.93\times10{-6}$ M of TQs were heated up to 95° C. and measured. The solutions were prepared by mixing equi-molar amounts of G-quadruplex (27.3 µL, $1.44\times10^{-4}$ M) with TQ compounds 1-8 (39.30 µL, $1\times10^{-4}$ M) in 1 mL KCl-buffer, pH 7.4. CD spectra were baseline corrected and CD intensities at 293 nm were plotted versus temperature.

Figure 5:
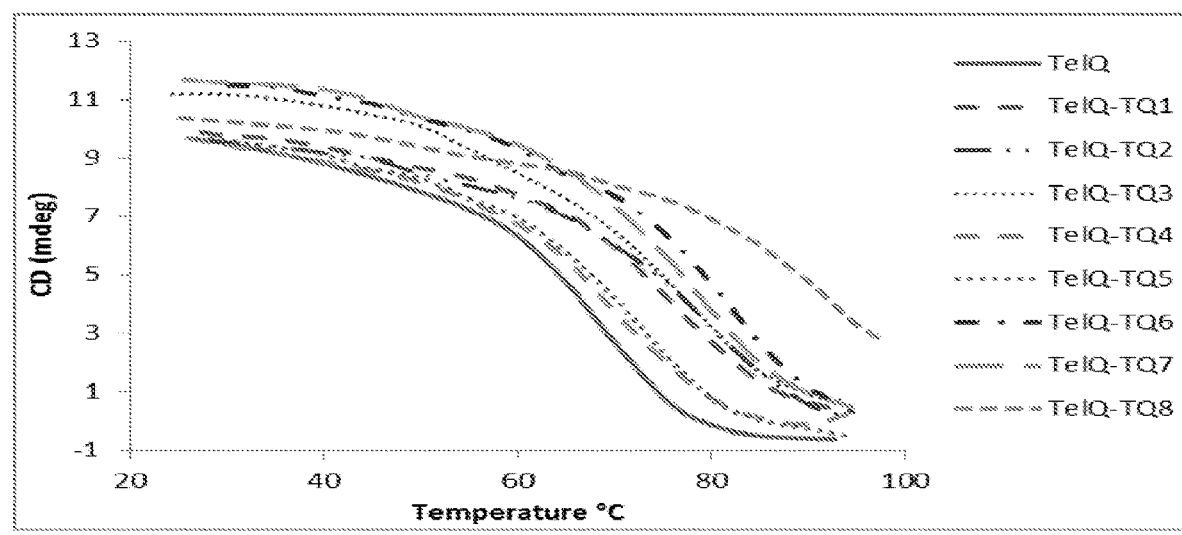
FIG. 5 shows the melting curve for G-quadruplex DNA and its complexes with compounds TQ1-8.

FIG. 5 shows the melting temperature curves for G-quadruplex and its TQs' complexes based on CD measurements. Table 3 shows the Tm values ranged between 70 and 91° C. for G-quadruplex DNA and its TQs complexes. These values reflected Tm ranges between 6.0° C. and 21° C. Compound TQ8 showed the highest Tm (91° C.) which is 21° C. higher than the G-quadruplex DNA.

These values are consistent with the binding constants shown in Table 3 and indicate that the compounds of the invention act as stabilizers for G-quadruplex DNA.

Binding Affinity

Scatchard plots were used to determine the binding affinity of the thymoquinone derivative compounds to G-quadruplex based on fluorescence titration, keeping the compounds concentration constant and varying DNA amounts.

Non-linear Scatchard plots were obtained for all TQ derivatives suggesting more than one type of dependant binding sites for all TQs molecules on G-quadruplex DNA molecule. Dependant binding sites may have synergistic (the first bound ligand encourage the next binding one) or antagonistic (the first bound ligand suppress the next binding one) effects on each other, a phenomenon known as the neighbor exclusion effect. Non-linear regression based on a modified Scatchard equation gave the binding constants and number of binding sites shown in Table 3. Compound TQ8 has shown the highest binding constant ($1.33 \times 10^7$ M$^{-1}$) and compound TQ5 has shown the lowest binding constant ($7.76 \times 10^4$ M$^{-1}$)

TABLE 3

Melting temperatures (Tm), binding constants (K) and number of binding sites (n) of G-quadruplex DNA upon interaction with various TQ derivative compounds (TQ1-8).

| Complex | Tm ° C. | Δ Tm ° C. | K (M$^{-1}$) | N |
| --- | --- | --- | --- | --- |
| G-quadruplex DNA | 70.0 | 0.00 | — | — |
| G-quadruplex DNA-TQ1 | 79.0 | 9.0 | $1.13 \times 10^5$ | 2 |
| G-quadruplex DNA-TQ2 | 76.0 | 6.0 | $5.67 \times 10^5$ | 1 |
| G-quadruplex DNA-TQ3 | 76.0 | 6.0 | $3.30 \times 10^5$ | 3 |
| G-quadruplex DNA-TQ4 | 76.0 | 6.0 | $9.52 \times 10^4$ | 3 |
| G-quadruplex DNA-TQ5 | 77.0 | 7.0 | $7.76 \times 10^4$ | 1 |
| G-quadruplex DNA-TQ6 | 80.0 | 10.0 | $1.49 \times 10^6$ | 2 |
| G-quadruplex DNA-TQ7 | 77.0 | 7.7 | $1.17 \times 10^6$ | 2 |
| G-quadruplex DNA-TQ8 | 91.0 | 21.0 | $1.33 \times 10^7$ | 2 |

Selectivity of TQs Towards G-Quadruplex

Selectivity of TQ derivative compounds towards G-quadruplex DNA was investigated using Fl-G-quadruplex (5'-Fl-AGGGTTAGGGTTAGGGTTAGGG-3') (SEQ ID NO:2) in presence of the telomeric dsDNA or ct-DNA as interfering species.

A 3 mL solution of TQ1-Fl-G-quadruplex complex was prepared by mixing 30.00 μl of Fl-G-quadruplex ($10^{-5}$ M) with 30 μl of TQ1 compound ($10^{-5}$ M). The solutions was made up to 3.00 ml using Tris-KCl-buffer pH 7.4, vortexed for 10 seconds, incubated for 3 minutes and then scanned for its fluorescence in the range 500-700 nm. The solution was then mixed with 0, 10, 50 or 100 folds of telomeric dsDNA or ct-DNA, vortexed for 10 seconds, incubated for 30 minutes at room temperature and scanned for its emission spectrum in the range 500-700 nm. The procedure was repeated for the TQ2-TQ8 compounds.

Figure 6:
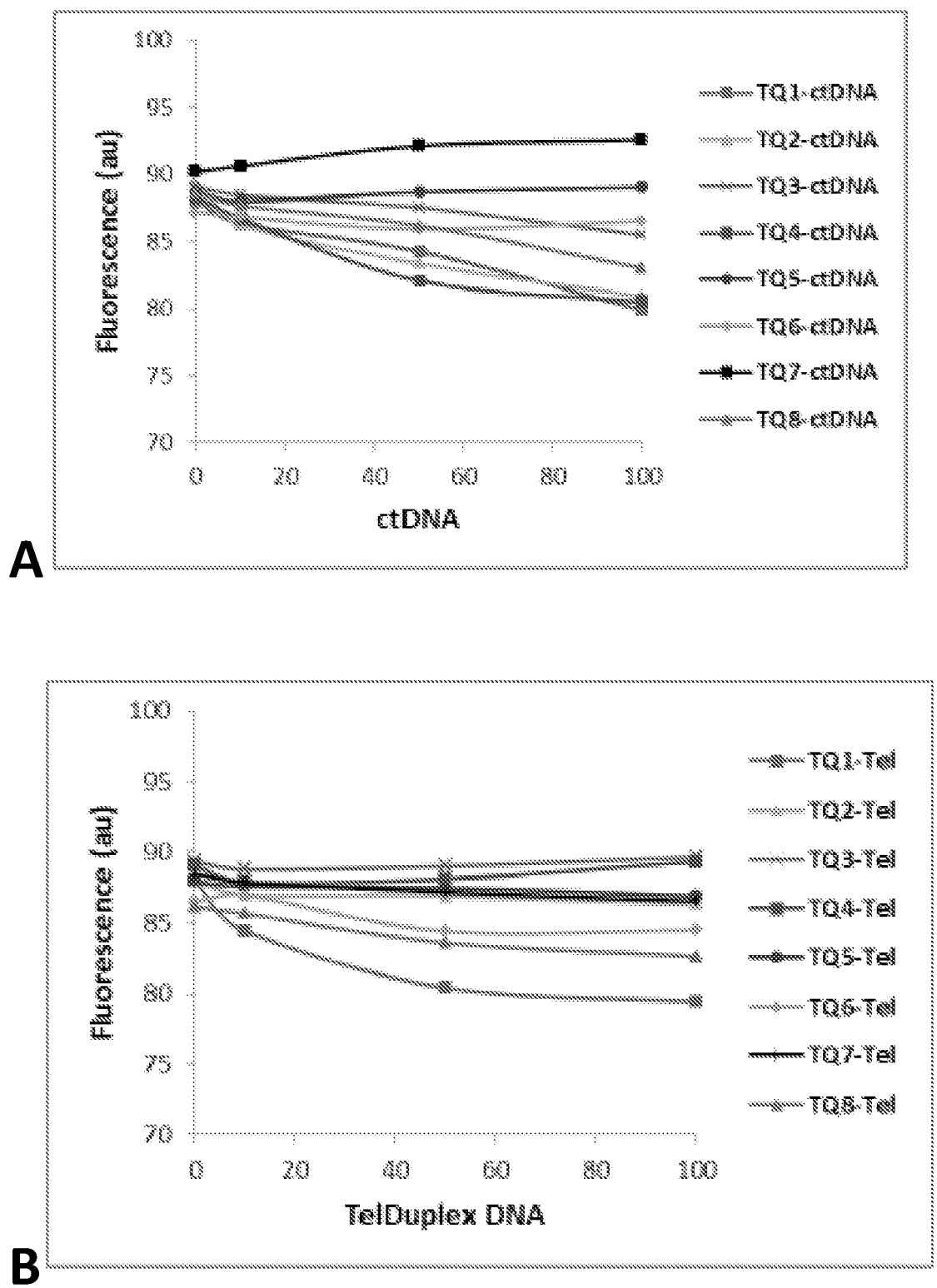
FIG. 6 shows the selectivity of compounds TQ1-8 toward G-quadruplex (5'-Flu-TelQ, 1×10−7 M) in presence of 0, 10, 50 and 100 folds of ct-DNA (A) and telomere dsDNA (B).

FIG. 6 shows change in fluorescence intensity of 5'-Fl-G-quadruplex TQs complexes in presence of 0, 10, 50 and 100 folds of ctDNA (FIG. 6a) and telomere dsDNA (FIG. 6b). The figures show that the fluorescence of 5'-Fl-G-TQs complexes are either constant or a slightly increased upon addition of ctDNA or telomere dsDNA indicating that both DNA species are non or slightly-interfering. These experiments indicate good selectivity for investigated thymoquinone compounds towards G-quadruplex DNA over ctDNA and telomere dsDNA.

These results indicate that the thymoquinone derivatives of the invention show good selectivity towards G-quadruplex DNA over duplex DNA and cytotoxicity over cancer cells, thereby suggesting that the compounds would be helpful in the treatment of cancers.

The invention claimed is:

1. A method of manufacturing a compound of formula (I):

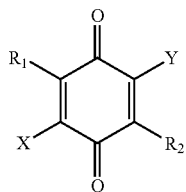

(I)

wherein
$R_1$ and $R_2$ are selected from methyl and isopropyl, wherein $R_1$ and $R_2$ are different;
X is $NR_3R_4$, wherein:
$R_3$ is selected from H or —$(CH_2)_2$—OH; and
$R_4$ is selected from H or —$(C_1$-$C_4$alkyl$)R_5$, wherein:
$R_5$ is selected from:
   a) —OH,
   b) phenyl substituted by 1-3 substituents independently selected from —$CF_3$, —F, —$OCH_3$, —$NH_2$ and —$SO_2NH_2$,
   c) a 5 or 6 membered heterocyclic ring having 1 or 2 hetero atoms selected from 0 and N, and wherein the heterocyclic ring is optionally substituted by 1-2 substituents independently selected from —OH and $CH_3$,
   d) a ring system having the formula of:

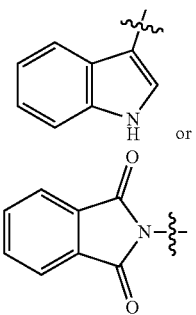

and
   e) $NR_6R_7$, wherein:
      $R_6$ is selected from H or $CH_3$; and
      $R_7$ is selected from $CH_3$, phenyl, and a ring system having the formula of:

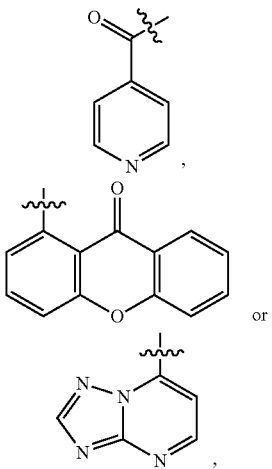

wherein the ring system is optionally substituted by 1-2 substituent of $CH_3$; and
Y is H,
the method of manufacturing the compound of formula (I) including reacting thymoquinone dissolved, at least partially, in a solvent for thymoquinone, with an amine of formula $NH_2R_3R_4$ dissolved, at least partially, in a solvent for said amine of formula $NH_2R_3R_4$, thereby to form a first compound of formula (I); and optionally hydrolyzing said first compound of formula (I) to form a second compound of formula (I).

2. The method of claim 1, wherein the solvent for thymoquinone is methanol.

3. The method of claim 1, wherein the thymoquinone and the amine of formula $NH_2R_3R_4$, are reacted in the presence of air.

4. The method of claim 1, wherein the thymoquinone and the amine of formula $NH_2R_3R_4$, are reacted at room temperature.

5. The method of claim 1, wherein the solvent for said amine of formula $NH_2R_3R_4$ is methanol.

6. The method of claim 1, wherein the solution containing the thymoquinone and the amine of formula $NH_2R_3R_4$ is concentrated and purified and the resultant products are crystallized.

7. The method of claim 1, wherein $R_1$ is methyl and $R_2$ is isopropyl.

8. The method of claim 1, wherein $R_3$ is H.

9. The method of claim 1, wherein $R_4$ is $(C_1-C_4alkyl)R_5$ and $R_5$ is selected from:
   a) —OH,
   b) phenyl substituted by 1-3 substituents independently selected from —$CF_3$, —F, —$OCH_3$, —$NH_2$ and —$SO_2NH_2$,
   c) a 5 or 6 membered heterocyclic ring selected from morpholinyl, pyranyl, piperidinyl, pyrrolidinyl, piperazinyl, pyridinyl, and pyrimidinyl, wherein the heterocyclic ring is optionally substituted by 1-2 substituents independently selected from —OH and $CH_3$,
   d) a ring system having the formula of:

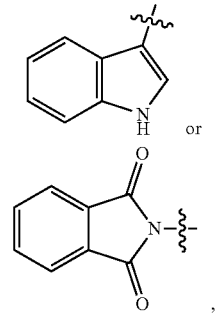

and
   e) $NR_6R_7$, wherein:
   $R_6$ is selected from H or $CH_3$; and
   $R_7$ is selected from $CH_3$, phenyl, and a ring system having the formula of:

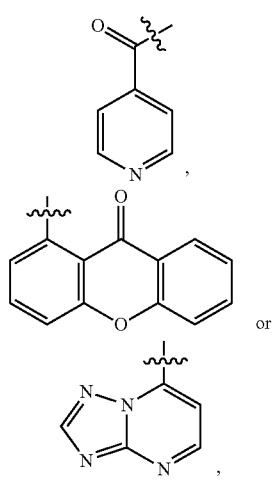

wherein the ring system is optionally substituted by 1-2 substituent of $CH_3$.

10. The method of claim 1, wherein $R_1$ is H or —$(C_1-C_4alkyl)R_5$, wherein $R_5$ is selected from OH, morpholinyl and phenyl, wherein the phenyl is optionally substituted with 1 or 2 substituents selected from —$CF_3$, —F and —$OCH_3$.

11. The method of claim 1, wherein the compound of Formula (I) is one of:
   5-Isopropyl-2-methyl-3-((2-morpholinoethyl)amino)-1,4-benzoquinone ($TQ_1$);
   5-Isopropyl-2-methyl-3-(4-trifluoromethylbenzylamino)-1,4-benzoquinone(TQ2);
   5-Isopropyl-2-methyl-3-(4-fluorobenzylamino)-1,4-benzoquinone ($TQ_3$);
   5-Isopropyl-2-methyl-3-(3,5-ditrifluoromethylbenzylamino)-1,4-benzoquinone ($TQ_5$);
   5-isopropyl-2-methyl-3-(2-hydroxyethylamino)-1,4-benzoquinone ($TQ_6$);
   5-isopropyl-2-methyl-3-(3,4-dimethoxybenzylamino)-1,4-benzoquinone (TQ7); and
   3-amino-5-isopropyl-2-methyl-1,4-benzoquinone (TQ8).

12. The method of claim 1, wherein the first compound of Formula (I) is one of:
   5-Isopropyl-2-methyl-3-((2-morpholinoethyl)amino)-1,4-benzoquinone ($TQ_1$);
   5-Isopropyl-2-methyl-3-(4-trifluoromethylbenzylamino)-1,4-benzoquinone(TQ2);
   5-Isopropyl-2-methyl-3-(4-fluorobenzylamino)-1,4-benzoquinone ($TQ_3$);
   5-Isopropyl-2-methyl-3-(3,5-ditrifluoromethylbenzylamino)-1,4-benzoquinone ($TQ_5$);
   5-isopropyl-2-methyl-3-(2-hydroxyethylamino)-1,4-benzoquinone ($TQ_6$); and
   5-isopropyl-2-methyl-3-(3,4-dimethoxybenzylamino)-1,4-benzoquinone ($TQ_7$).

13. The method of claim 1, wherein the first compound of Formula (I) is 5-isopropyl-2-methyl-3-(3,4-dimethoxybenzylamino)-1,4-benzoquinone (TQ7); and the second compound of Formula (I) is 3-amino-5-isopropyl-2-methyl-1,4-benzoquinone ($TQ_8$).

14. The method of claim 1, wherein the first compound of Formula (I) is 5-Isopropyl-2-methyl-3-((2-morpholinoethyl)amino)-1,4-benzoquinone ($TQ_1$).

15. The method of claim 1, wherein the first compound of Formula (I) is 5-Isopropyl-2-methyl-3-(4-trifluoromethylbenzylamino)-1,4-benzoquinone($TQ_2$).

16. The method of claim 1, wherein the first compound of Formula (I) is 5-Isopropyl-2-methyl-3-(4-fluorobenzylamino)-1,4-benzoquinone (TQ3).

17. The method of claim 1, wherein the first compound of Formula (I) is 5-Isopropyl-2-methyl-3-(3,5-ditrifluoromethylbenzylamino)-1,4-benzoquinone (TQ5).

18. The method of claim 1, wherein the first compound of Formula (I) is 5-isopropyl-2-methyl-3-(2-hydroxyethylamino)-1,4-benzoquinone ($TQ_6$).

19. The method of claim 1, wherein the first compound of Formula (I) is 5-isopropyl-2-methyl-3-(3,4-dimethoxybenzylamino)-1,4-benzoquinone (TQ7).

* * * * *

SEQUENCE LISTING

<160> NUMBER OF SEQ ID NOS: 3

<210> SEQ ID NO 1
<211> LENGTH: 22
<212> TYPE: DNA
<213> ORGANISM: Homo sapiens

<400> SEQUENCE: 1
agggttaggg ttagggttag gg                                                 22

<210> SEQ ID NO 2
<211> LENGTH: 22
<212> TYPE: DNA
<213> ORGANISM: Homo sapiens

```
<220> FEATURE:
<221> NAME/KEY: misc_feature
<223> OTHER INFORMATION: Fluorescein label
<220> FEATURE:
<221> NAME/KEY: misc_feature
<222> LOCATION: (1)..(1)
<223> OTHER INFORMATION: Fluorescein label

<400> SEQUENCE: 2
agggttaggg ttagggttag gg                                              22

<210> SEQ ID NO 3
<211> LENGTH: 22
<212> TYPE: DNA
<213> ORGANISM: Homo sapiens

<400> SEQUENCE: 3
ccctaaccct aaccctaacc ct                                              22
```